United States Patent [19]

Lesieur et al.

[11] Patent Number: 5,693,665

[45] Date of Patent: Dec. 2, 1997

[54] ALKYLATED (HETERO) CYCLIC COMPOUNDS

[75] Inventors: Daniel Lesieur, Gondecourt; Eric Fourmaintraux, St Martin/Boulogne S/Mer; Patrick Depreux, Armentieres; Philippe Delagrange, Issy-les-Moulineaux; Pierre Renard, Versailles; Béatrice Guardiola-Lemaitre, Saint-Cloud, all of France

[73] Assignee: Adir et Compagnie, Courbevoie, France

[21] Appl. No.: 584,465

[22] Filed: Jan. 10, 1996

[30] Foreign Application Priority Data

Jan. 11, 1995 [FR] France .................... 95 00238

[51] Int. Cl.[6] ........................ A61K 31/38; C07D 335/06
[52] U.S. Cl. ................................. 514/443; 549/58
[58] Field of Search .................... 514/443; 549/58

[56] References Cited

PUBLICATIONS

CA 123: 330021 Inhibitors of the ... muscle mass. Stein et al., 1995.

*Primary Examiner*—Joseph McKane
*Attorney, Agent, or Firm*—The Firm of Gordon W. Hueschen

[57] ABSTRACT

The invention relates to a compounds selected from these of formula (I):

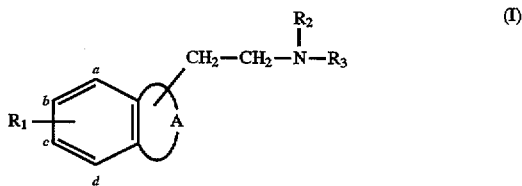

in which: $R_1$, $R_2$, $R_3$ and A are as defined in the description, and a medicinal product containing the same useful for treating a melatoninergic disorder.

14 Claims, No Drawings

ALKYLATED (HETERO) CYCLIC COMPOUNDS

The invention relates to novel alkylated (hetero)cyclic compounds, to a process for their preparation and to the pharmaceutical compositions which contain them.

The invention describes novel alkylated (hetero)cyclic compounds which prove to be powerful ligands for melatoninergic receptors.

In the last ten years, many studies have demonstrated the fundamental role of melatonin (5-methoxy-N-acetyltryptamine) in controlling circadian rhythm and endocrine functions, and the melatonin receptors have been characterized and localized.

Besides their beneficial action on disorders of circadian rhythm (J. Neurosurg., 1985, 63, pp 321–341) and on sleeping disorders (Psychopharmacology, 1990, 100, pp 222–226), ligands for the melatoninergic system possess advantageous pharmacological properties with regard to the central nervous system, in particular anxiolytic and antipsychotic properties (Neuropharmacology of Pineal Secretions, 1990, 8 (3–4), pp 264–272) and analgesic properties (Pharmacopsychiat., 1987, 20, pp 222–223) as well as for the treatment of Parkinson's disease (J. Neurosurg., 1985, 63, pp 321–341) and Alzheimer's disease (Brain Research, 1990, 528, pp 170–174). Similarly, these compounds have shown an activity on certain cancers (Melatonin - clinical Perspectives, Oxford University Press, 1988, page 164–165), on ovulation (Science 1987, 227, pp 714–720), and on diabetes (Clinical endocrinology, 1986, 24, pp 359–364).

Compounds which make it possible to act on the melatoninergic system are thus excellent medicinal products, for clinicians, for the treatment of the pathologies mentioned above.

The invention relates to the compounds of formula (I):

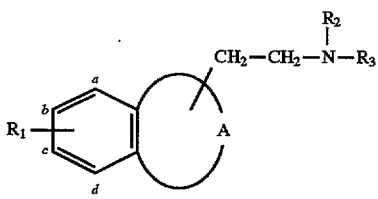

in which:

$R_1$ represents a radical chosen from alkyl, substituted alkyl, cycloalkyl, substituted cycloalkyl, cycloalkylalkyl and substituted cycloalkylalkyl, A forms, with the benzene ring to which it is attached, a cyclic group chosen from tetrahydronaphthalene, dihydronaphthalene, naphthalene, benzothiophene, 2,3-dihydrobenzothiophene, indoline, substituted indoline, indole and substituted indole, $R_2$ represents a hydrogen or an alkyl, $R_3$ represents:

a group $R_{31}$:

with X representing a sulfur or an oxygen and $R_4$ representing a hydrogen or a radical $R_{41}$ chosen from alkyl, substituted alkyl, alkenyl, alkynyl, cycloalkyl, substituted cycloalkyl, cycloalkylalkyl and substituted cycloalkylalkyl, or a group of formula ($R_{32}$):

with X' representing a sulfur or an oxygen and $R_5$ representing a hydrogen or a radical chosen from alkyl, substituted alkyl, cycloalkyl, substituted cycloalkyl, cycloalkylalkyl and substituted cycloalkylalkyl, it being understood that in the description of formula (I), and except where otherwise mentioned:

the terms "alkyl" and "alkoxy" denote linear or branched groups containing from 1 to 6 carbon atoms, the terms "alkenyl" and "alkynyl" denote linear or branched groups containing from 2 to 6 atoms, the term "cycloalkyl" denotes a group of 3 to 8 carbon atoms, the term "substituted" associated with the alkyl radical means that this radical is substituted with one or more substituents chosen from halogen, "alkyl", hydroxyl and alkoxy, the term "substituted" associated with the "cycloalkyl" and "cycloalkylalkyl" radicals means that this radical is substituted with one or more radicals or groups chosen from halogen, alkyl and oxo, the term "substituted" associated with the terms "indole" and "indoline" means that these groups are substituted on the nitrogen in the 1-position with a radical chosen from —Ra, —CO—Ra and —CO—O—Ra in which Ra represents an alkyl, phenyl or phenylalkyl radical, and the enantiomers and diastereoisomers thereof.

The invention relates more particularly to the compounds of formula (I) in which, taken separately or together, $R_1$ represents an alkyl, $R_1$ represents a ($C_2$-$C_6$)alkyl, $R_1$ represents an ethyl, $R_1$ represents a propyl, $R_1$ represents a butyl, A forms with the benzene ring to which it is attached, a tetrahydronaphthalene, A forms with the benzene ring to which it is attached a naphthalene, A forms with the benzene ring to which it is attached a dihydronaphthalene, A forms with the benzene ring to which it is attached a benzothiophene, A forms with the benzene ring to which it is attached an indole, A forms with the benzene ring to which it is attached a substituted indole, $R_2$ represents a hydrogen, $R_2$ represents an alkyl, $R_3$ represents a group $R_{31}$ as defined in formula (I), $R_3$ represents a group $R_{32}$ as defined in formula (I), $R_4$ represents a hydrogen atom, $R_4$ represents an alkyl, $R_4$ represents a cycloalkyl, $R_4$ represents an alkenyl, $R_5$ represents a hydrogen, $R_5$ represents an alkyl, $R_5$ represents a cycloalkyl, X represents an oxygen, X represents a sulfur, X' represents an oxygen, or X' represents a sulfur.

For example, the invention relates to the specific compounds of formula (I) corresponding to the respective formulae (1) to (5):

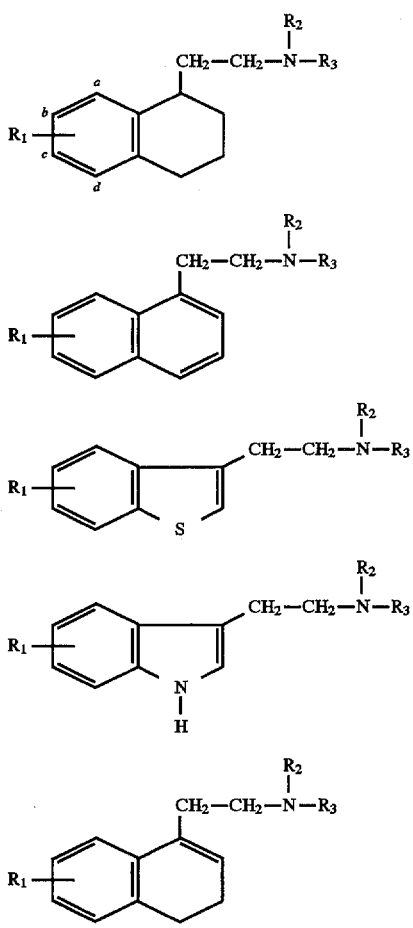

The invention relates particularly to the compounds of formula (I), for example the specific compounds of formulae (1) to (5), as defined above in which $R_1$ is:
in position a of the benzene ring,
in position b of the benzene ring,
in position c of the benzene ring,
or in position d of the benzene ring.

For example, the invention relates to the compounds of formula (I) in which $R_1$ is in position b of the benzo ring.

The invention specifically relates to the following compounds:
N-[2-(5-ethylbenzothiophen-3-yl)ethyl]acetamide,
N-[2-(5-ethylbenzothiophen-3-yl)ethyl]cyclobutanecarboxamide,
N-[2-(7-ethyl-1,2,3,4-tetrahydronaphth-1-yl)ethyl]acetamide,
N-[2-(7-ethyl- 1,2,3,4-tetrahydronaphth-1-yl)ethyl]butyramide,
N-[2-(7-ethyl-1,2,3,4-tetrahydronaphth-1-yl)ethyl]cyclopropanecarboxamide,
N-[2-(7-ethyl-1,2,3,4-tetrahydronaphth-1-yl)ethyl]pentanamide,
and N-[2-(7-ethyl-1,2,3,4-tetrahydronaphth-1-yl)ethyl]trifluoroacetamide.

The alkyl radicals present in formula (I) may specifically be chosen from methyl, ethyl, n-propyl, isopropyl, n-butyl, isobutyl, sec-butyl, tert-butyl, pentyl and hexyl.

The alkoxy radicals present in formula (I) may be chosen from methoxy, ethoxy, n-propoxy, isopropoxy, n-butoxy, isobutoxy, sec-butoxy, tert-butoxy, pentyloxy and hexyloxy.

The halogens present in formula (I) may be chosen from bromine, chlorine, fluorine and iodine.

The cycloalkyls present in formula (I) may be chosen from cyclopropyl, cyclobutyl, cyclopentyl, cyclohexyl, cycloheptyl and cyclooctyl.

The invention also relates to the process for the preparation of the compounds of formula (I), wherein:
a compound of formula (II):

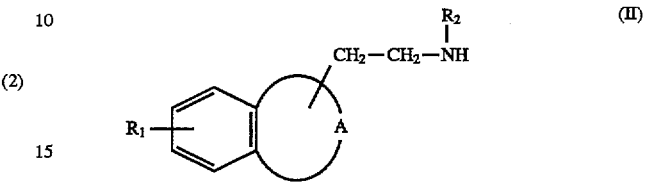

in which $R_1$ and A are as defined in formula (I), is reacted either with formic acid or with a compound of formula (IIIa) or (IIIb):

in which $R_{41}$ is as defined in formula (I) and Hal represents a halogen, in order to obtain the compounds of formula (I/a):

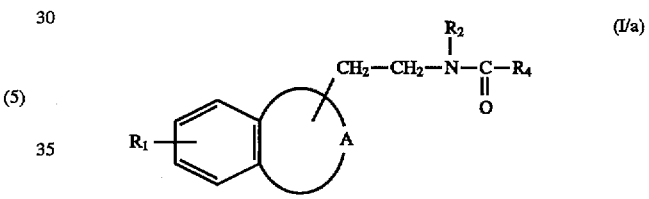

in which $R_1$, $R_2$, $R_4$ and A are as defined above, which compounds of formula (I/a) are treated with Lawesson's reagent in order to obtain the compounds of formula (I/a'):

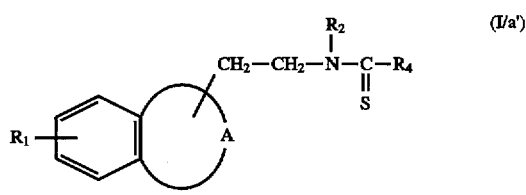

in which $R_1$, $R_2$, $R_4$ and A are as defined above,
or with a compound of formula (IV):

in which X' and $R_5$ are as defined in formula (I) in order to obtain the compounds of formula (I/b):

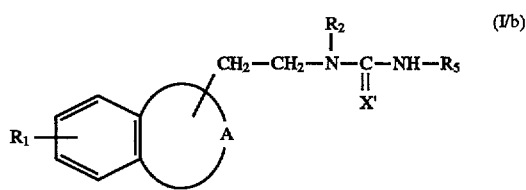

in which $R_1$, $R_2$, $R_5$, A and X' are as defined above, the compounds of formulae (I/a), (I/a') and (I/b) forming the set of compounds of formula (I), which compounds of formula (I) are, where appropriate, separated into the various enantiomers or diastereoisomers thereof.

For example, the invention covers the process for the preparation of the compounds of formula (I/c):

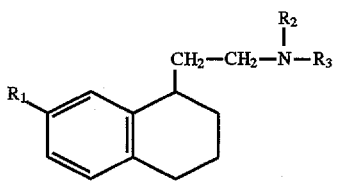

in which $R_1$, $R_2$ and $R_3$ are as defined in formula (I), wherein:
a compound of formula (II/a):

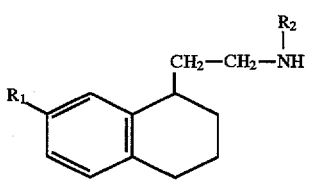

in which $R_1$ and $R_2$ are defined as above, is reacted
either with a compound of formula (IIIa) or (IIIb) as defined above, in order to obtain the compounds of formula (I/d):

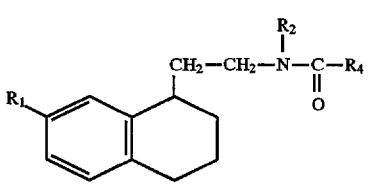

in which $R_1$, $R_2$ and $R_4$ are as defined above, which compounds are then treated with Lawesson's reagent in order to obtain the compounds of formula (I/d'):

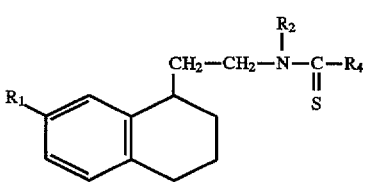

in which $R_1$, $R_2$ and $R_4$ are as defined above,
or with a compound of formula (IV) as defined above, in order to obtain the compounds of formula (I/e):

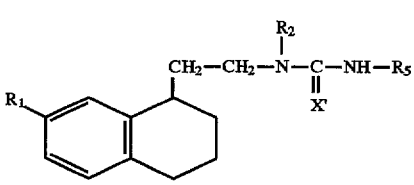

in which $R_1$, $R_2$, $R_5$ and X' are as defined above, the compounds of formula (I/d), (I/d') and (I/e) forming the set of compounds of formula (I/c), it being possible for the compounds of formula (I/c) to be separated into the various enantiomers or diastereoisomers thereof.

For example, the invention also covers the process for the preparation of the compounds of formula (I/f):

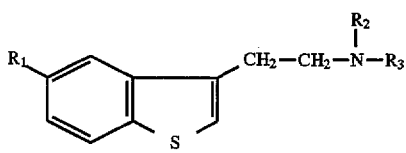

in which $R_1$, $R_2$ and $R_3$ are as defined in formula (I), wherein:
a compound of formula (II/b):

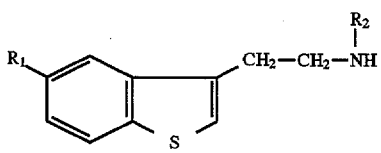

in which $R_1$ and $R_2$ are as defined above, is reacted
either with a compound of formula (IIIa) or (IIIb) as defined above, in order to obtain the compounds of formula (I/g):

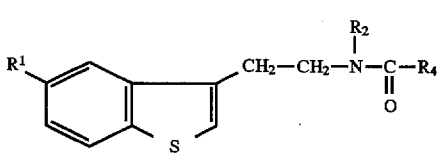

in which $R_1$, $R_2$ and $R_4$ are as defined above, which compounds are then treated with Lawesson's reagent in order to obtain the compounds of formula (I/g'):

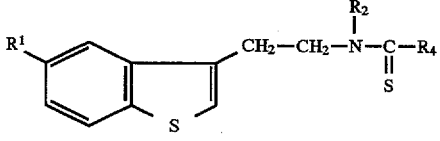

in which $R_1$, $R_2$ and $R_4$ are as defined above,
or with a compound of formula (IV) as defined above, in order to obtain the compounds of formula (I/h):

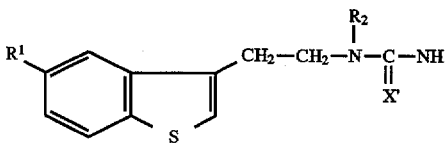

in which $R_1$, $R_2$, $R_5$ and X' are as defined above,
the compounds of formula (I/g), (I/g') and (I/h) forming the set of compounds of formula (I/f), it being possible for the compounds of formula (I/f) to be separated into the various enantiomers or diastereoisomers thereof.

The starting materials used in the processes described above are either commercial or are readily accessible to those skilled in the art by means of the literature and the preparation examples given below.

For example, it is possible to prepare the compounds of formula (II/a):

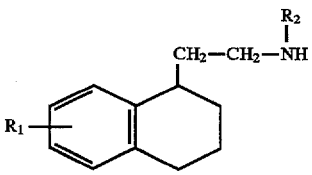

in which $R_1$ and $R_2$ are as defined in formula (I), by reaction of a compound of formula (V):

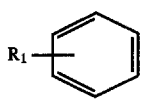

in which $R_1$ is as defined above, with succinic anhydride in order to obtain a compound of formula (VI):

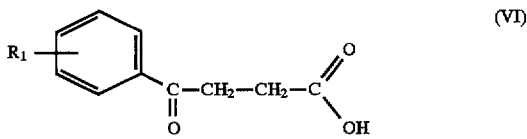

in which $R_1$ is as defined above, which compound is reduced in order to obtain a compound of formula (VII):

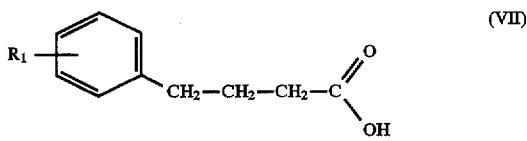

in which $R_1$ is as defined above, which compound is then cyclized in order to obtain a compound of formula (VIII):

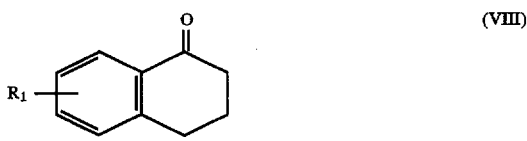

in which $R_1$ is as defined above, which compound is reacted with diethyl cyanomethyl phosphonate in order to obtain the compound of formula (IX):

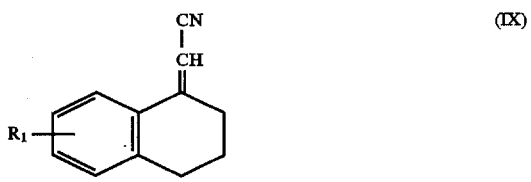

in which $R_1$ is as defined above, which compound is then hydrogenated in order to obtain the compound of formula (II/c):

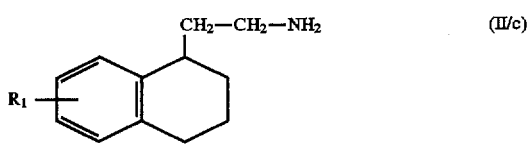

in which $R_1$ is as defined above, which compound of formula (II/c) is optionally alkylated on the amine function in order to obtain a compound of formula (II/d):

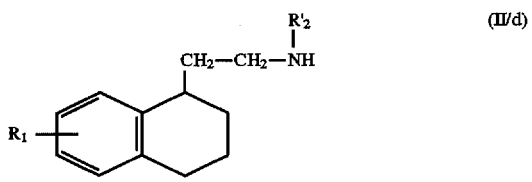

in which $R_1$ is as defined above and $R'_2$ represents a $(C_1-C_6)$alkyl radical, the compounds of formulae (II/c) and (II/d) forming the set of compounds of formula (II/a), it being possible for the compounds of formula (II/ a) to be separated into the enantiomers or diastereoisomers thereof and salified with a pharmaceutically acceptable acid.

The aromatization of the compounds of tetrahydronaphthalene structure as described above makes it possible to obtain compounds which are useful for the preparation of the compounds of formula (I) in which A forms, with the benzene ring to which it is attached, a naphthalene ring.

Another preparation example for the compounds of formula (II) consists in the process for the preparation of the compounds of formula (II/e):

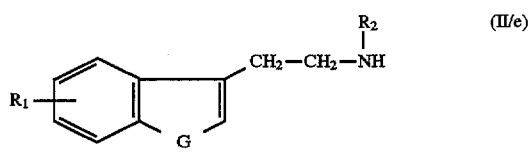

in which $R_1$ and $R_2$ are as defined in formula (I) and G represents a sulfur or an —NH group, wherein a compound of formula (X):

in which $R_1$ and G are as defined above, is reacted with ethyl 4-chloroacetoacetate in order to obtain the compound of formula (XI):

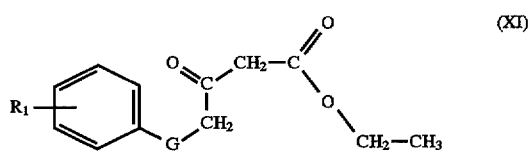

in which $R_1$ and G are as defined above, which compound is cyclized in order to obtain a compound of formula (XII),

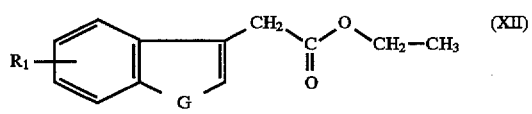

in which $R_1$ and G are as defined above, which compound is hydrolyzed in order to obtain the compound of formula (XIII):

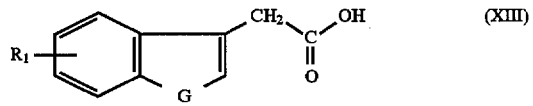

in which $R_1$ and G are as defined above, which compound is amidated in order to obtain a compound of formula (XIV):

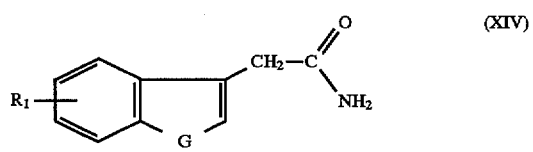

in which $R_1$ and G are as defined above, which compound is dehydrated to the nitrile and then reduced in order to obtain a compound of formula (II/f):

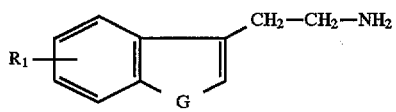

in which $R_1$ and G are as defined above, which compound of formula (II/e) is optionally alkylated on the amine function in order to obtain a compound of formula (II/g):

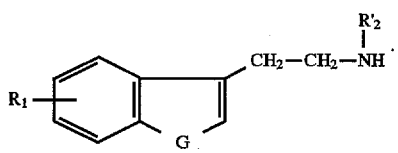

in which $R_1$ and G are as defined above and $R'_2$ represents a $(C_1-C_6)$alkyl radical, the compounds of formulae (II/f) and (II/g) forming the set of compounds of formula (II/d), it being possible for the compounds of formula (II/e) to be salified with a pharmaceutically acceptable acid.

More particularly, the preparation of the compounds of formula (II/d) is accessible when G represents a sulfur.

Among the pharmaceutically acceptable acids which may be used to form an addition salt with the compounds of formula (II), there may be mentioned, by way of non-limiting examples, hydrochloric acid, sulfuric acid, phosphoric acid, tartaric acid, malic acid, maleic acid, fumaric acid, oxalic acid, methanesulfonic acid, ethanesulfonic acid, camphoric acid and citric acid.

The compounds of formula (I) possess pharmacological properties which are very advantageous for clinicians.

The compounds of the invention and the pharmaceutical compositions containing them prove to be useful for the treatment of disorders of the melatoninergic system.

Pharmacological study of the compounds of the invention has indeed shown that they were not toxic, were endowed with a very selective affinity for the melatonin receptors and had considerable activities on the central nervous system and, in particular, therapeutic properties with regard to sleeping disorders, anxiolytic, antipsychotic and analgesic properties were found, as well as therapeutic properties with regard to microcirculation, which make it possible to establish that the products of the invention are useful in the treatment of stress, sleeping disorders, anxiety, seasonal depressions, cardiovascular pathologies, insomnia and fatigue due to changes in time zone, schizophrenia, panic attacks, melancholia, appetite disorders, obesity, insomnia, psychotic disorders, epilepsy, Parkinson's disease, senile dementia, various disorders associated with normal or pathological ageing, migraine, memory loss, Alzheimer's disease, and disorders of cerebral circulation. In another field of activity, it is seen that the products of the invention possess immunomodulatory and ovulation-inhibitory properties and that they can be used in anticancer treatment.

The compounds will preferably be used in the treatment of seasonal depressions, sleeping disorders, cardiovascular pathologies, insomnia and fatigue due to changes in time zone, appetite disorders and obesity.

For example, the compounds will be used in the treatment of seasonal depressions and sleeping disorders.

Another subject of the present invention is the pharmaceutical compositions containing the products of formula (I) in combination with one or more pharmaceutically acceptable excipients.

Among the pharmaceutical compositions according to the invention which may be mentioned more particularly are those which are suitable for oral, parenteral, nasal per- or transcutaneous, rectal, perlingual, ocular or respiratory administration, and in particular simple or coated tablets, sublingual tablets, sachets, packets, gelatin capsules, glossettes, lozenges, suppositories, creams, salves, derreal gels, and drinkable or injectable ampules.

The dosage varies depending on the sex, age and weight of the patient, the route of administration, the nature of the therapeutic indication, or on treatments which may be associated, and is graded between 0.1 mg and 1 g per 24 hours taken in 1 or 2 doses, more particularly between 1 and 100 mg, for example between 1 and 10 mg.

The examples which follow illustrate the invention, but do not limit it in any way.

PREPARATION 1: 2-(7-ETHYL-1,2,3-4-TETRAHYDRONAPHTH-1-YL)ETHYLAMINE

STAGE A: 4-OXO-4-(4-ETHYLPHENYL)BUTYRIC ACID

Reactants:
Ethylbenzene: 0.05 mol (5 cm$^3$)
Aluminum chloride: 0.02 mol (2.6 g)
Succinic anhydride: 0.01 mol (1 g)
Procedure:

5 cm$^3$ of ethylbenzene and 2.6 g of aluminum chloride are mixed together with magnetic stirring in a 50 cm$^3$ flask. The solution is cooled in an ice bath and 1 g of succinic anhydride is then added. The mixture is stirred for 1 h 30 at a temperature of 0° C. and then for 3 h at room temperature. The reaction mixture is poured into ice. This mixture is acidified by addition of 1N hydrochloric acid (pH 3–4). It is extracted with 3 volumes of ether. The organic phases are washed 3 times with 10% potassium carbonate solution. The aqueous phases are combined and acidified by addition of concentrated hydrochloric acid. The precipitate obtained is drained and then recrystallized.

Characteristics:
206.23 g/mol for $C_{12}H_{14}O_3$
White powder
Melting point: 106°–108° C.
Rf=0.36; eluent: acetone/toluene/cyclohexane (2/2/1)
Recrystallization solvent: cyclohexane
Yield: 57%

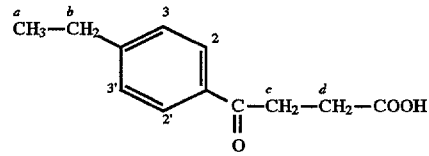

Infrared spectroscopy analysis:
2960–2920 cm$^{-1}$: $\upsilon$CH alkyl
1710 cm$^{-1}$: $\upsilon$CO acid
1670 cm$^{-1}$: $\upsilon$CO ketone
1600 cm$^{-1}$: $\upsilon$C=C aromatic
Proton NMR spectroscopic analysis (80 MHz, DMSO-d$_6$, $\delta$):
1.2 ppm (triplet, 3H): CH$_3$(a) J$_{a-b}$=6.60 Hz
2.6 ppm (multiplet,4H): CH$_2$(b) and CH$_2$(d) Jb-a=Jd-c= 6.60 Hz
3.2 ppm (triplet, 2H): CH$_2$(c) Jc-d=6.60 Hz
7.4 ppm (doublet, 2H): H$_3$ and H$_5$ J$_{ortho}$=8.80 Hz
7.9 ppm (doublet, 2H): H$_2$ and H$_6$ J$_{ortho}$=8.80 Hz
12.1 ppm (multiplet, 1H): COOH
Mass spectrometric analysis:
m/e 206: M$^+$
m/e 207: (M+1)$^+$

STAGE B: 4-(4-ETHYLPHENYL)BUTYRIC ACID

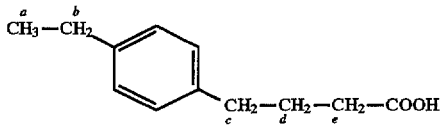

Reactants:
  4-Oxo-4-(4-ethylphenyl)butyric acid (Stage A): 0.012 mol (2.5 g)
  Triethylsilane: 0.028 mol (3.2 g)
  Trifluoroacetic acid: 0.12 mol (19 cm³)

Procedure:

2.5 g of 4-oxo-4-(4-ethylphenyl)butyric acid are dissolved in 19 cm³ of trifluoroacetic acid with magnetic stirring in a 100 cm³ flask. 3.2 g of triethylsilane are added dropwise. The mixture is stirred for 86 hours at room temperature. The reaction mixture is poured into ice. It is extracted with 3 volumes of ether. The organic phases are washed 3 times with 10% potassium carbonate solution. The aqueous phases are combined and then acidified by addition of concentrated hydrochloric acid, to pH 3–4. The precipitate obtained is drained and then recrystallized.

Characteristics:
  192.25 g/mol for $C_{12}H_{16}O$
  White powder
  Melting point: 71°–73° C.
  Rf=0.67, eluent: acetone/toluene/cyclohexane (2/2/1)
  Recrystallization solvent: water
  Yield: 65%

Infrared spectroscopic analysis:
  3280–2780 cm⁻¹: υOH acid
  2940–2850 cm⁻¹: υCH alkyl
  1680 cm⁻¹: υCO acid
  1510 cm⁻¹: υC=C aromatic Proton NMR spectroscopic analysis (300 MHz, DMSO-d₆, δ):
  1.14 ppm (triplet, 3H): $CH_3$(a) $J_{a\text{-}b}$=7.63 Hz
  1.76 ppm (multiplet, 2H): $CH_2$(d)
  2.20 ppm (triplet, 2H): $CH_2$(e) $J_{d\text{-}e}$=7.65 Hz
  2.55 ppm (multiplet, 4H): $CH_2$(c) and $CH_2$(b)
  7.11 ppm (multiplet, 6H): aromatic H
  Acidic OH not observed Mass spectrometric analysis:
  m/e 192: M⁺
  m/e 193: (M+1)⁺

STAGE C: 7-ETHYL-1-TETRALONE

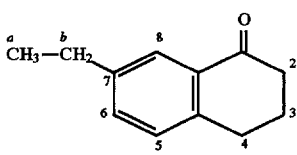

Reactants:
  4-(4-Ethylphenyl)butyric acid (Stage B): 0.013 mol (2,5 g) Polyphosphoric acid: 25 g Procedure:

25 g of polyphosphoric acid are poured into a 100 cm³ ground-necked round-bottomed flask. 2.5 g of 4-(4-ethylphenyl)butyric acid are added. The mixture is stirred for 6 h at a temperature of 45° C. The reaction mixture is poured into ice. It is extracted with 3 volumes of ether. The organic phases are washed 3 times with 10% potassium carbonate solution, dried over magnesium sulfate and then evaporated to dryness.

The oil obtained is purified by column chromatography.

Characteristics:
  174.23 g/mol for $C_{12}H_{14}O_2$
  Colorless oil
  Rf=0.35 eluent: toluene/cyclohexane (½)
  Yield: 55%

Infrared spectroscopic analysis:
  3010 cm⁻¹: υCH aromatic
  2980–2860 cm⁻¹: υCH alkyl
  1680 cm⁻¹: υCO ketone
  1605 cm⁻¹: υC=C aromatic Proton NMR spectroscopic analysis (300 MHz, DMSO-d₆, δ):
  1.13 ppm (triplet, 3H): $CH_3$(a), $J_{a\text{-}b}$=7.68 Hz
  2.01 ppm (multiplet, 2H): $CH_2$(3)
  2.59 ppm (multiplet, 4H): $CH_2$(b) and $CH_2$(4)
  2.88 ppm (triplet, 2H): $CH_2$(2), $J_{2\text{-}3}$=5.77 Hz
  7.25 ppm (doublet, 1H): $H_5$, $J_{ortho}$=8.59 Hz
  7.39 ppm (doubled doublet, 1H) $H_6$, $J_{ortho}$=8.59 Hz, $J_{meta}$=2.14 Hz
  7.70 ppm (doublet, 1H) $H_8$, $J_{meta}$=2.14 Hz Mass spectrometric analysis:
  m/e 174:M⁺
  m/e 175:(M+1)⁺

STAGE D: 2-(7-ETHYL-1,2,3,4-TETRAHYDRO-NAPHTHYLIDEN-1-YL)ACETONITRILE

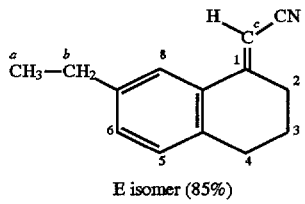

E isomer (85%)

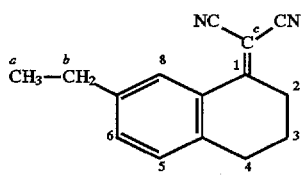

Z isomer (15%)

Reactants:
  7-Ethyltetralone (Stage C): 0.029 mol (5 g)
  Diethyl cyanomethyl phosphonate: 0.048 mol (8.9 g)
  Sodium hydride: 0.048 mol (1.12 g)
  Anhydrous tetrahydrofuran: 20 cm³

Procedure:

Nitrogen gas is sparged into 20 cm³ of anhydrous tetrahydrofuran in a 100 cm³ three-necked round-bottomed flask. 1.15 g of sodium hydride are added with magnetic stirring, followed by dropwise addition of diethyl cyanomethyl phosphonate. The reaction medium is stirred for 1 h at room temperature, until the evolution of gas ceases. The 7-ethyltetralone is added and stirring is continued for 24 h at room temperature, under a stream of nitrogen gas. The reaction mixture is poured into ice. It is extracted with 3 volumes of ether. The organic phases are washed 3 times with water, dried over magnesium sulfate and then evaporated to dryness. The oil obtained is purified by column chromatography.

Characteristics:
  197.27 g/mol for $C_{14}H_{15}N$
  Colorless oil
  Rf=0.60, eluent: acetone/toluene/cyclohexane (5/3/2)
  Yield: 60%

Infrared spectroscopic analysis:
- 3050 cm$^{-1}$: υCH aromatic
- 2960–2820 cm$^{-1}$: υCH alky
- 2200 cm$^{-1}$: υCN
- 1585 cm$^{-1}$: υC=C aromatic Proton NMR spectroscopic analysis (300 MHz, DMSO-d$_6$, δ):

E Isomer:
- 1.22 ppm (triplet, 3H): CH$_3$(a), J$_{a-b}$=8.04 Hz
- 1.94 ppm (multiplet, 2H): CH$_2$(3)
- 2.66 ppm (multiplet, 2H): CH$_2$(2)
- 2.87 ppm (multiplet, 4H): CH$_2$(b) and CH$_2$ (4)
- 5.73 ppm (singlet, 1H): CH (c)
- 7.08 ppm (doublet, 1H): H$_5$, J$_{ortho}$=7.76 Hz
- 7.16 ppm (multiplet, 1H): H$_6$, J$_{ortho}$=7.76 Hz
- 7.36 ppm (multiplet, 1H): H$_8$ Z Isormer
- 1.22 ppm (triplet 3H): CH$_3$(a), J$_{a-b}$=8.04 Hz
- 1.94 ppm (multiplet, 2H): CH$_2$(3)
- 2.66 ppm (multiplet, 2H): CH$_2$(2)
- 2.87 ppm (multiplet, 4H): CH$_2$(b) and CH$_2$(4)
- 5.23 ppm (singlet, 1H): CH (c)
- 7.08 ppm (doublet, 1H): H$_5$, J$_{ortho}$=7.76 Hz
- 7.16 ppm (multiplet, 1H): H$_6$, J$_{ortho}$=7.76 Hz
- 8.14 ppm (multiplet, 1H): H$_8$

STAGE E: (R,S) 2-(7-ETHYL-1,2,3,4-TETRAHYDRONAPHTH-1-YL)ETHYLAMINE

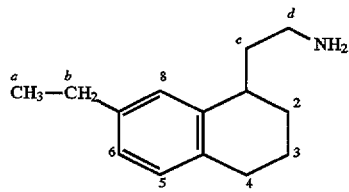

Reactants:
- 2-(7-Ethyl-1,2,3,4-tetrahydronaphthyliden-1-yl) acetonitrile (Stage D): 0.015 mol (3 g)
- Absolute alcohol: 150 cm$^3$
- Raney nickel: 0.5 g
- Hydrogen: 60 bar Procedure:

3 g of 2-(7-ethyl-1,2,3,4-tetrahydronaphthyliden-1-yl) acetonitrile are dissolved in 150 cm$^3$ of absolute alcohol in a 250 cm$^3$ autoclave. 0.5 g of Raney nickel is added. The mixture is stirred for 6 h at 60° C. under a hydrogen pressure of 60 bar. The mixture is filtered under vacuum. The filtrate is evaporated to dryness. The residue is taken up in a small volume of ether saturated with gaseous hydrogen chloride. The precipitate which forms is drained and then recrystallized.

Characteristics (hydrochloride):
- 239.78 g/mol for C$_{14}$H$_{22}$ClN
- White powder
- Melting point:: 116°–118° C.
- Rf=0.73, in acetone/toluene/cyclohexane/triethylamine (5/3/2/1)
- Yield: 49%
- Recrystallization solvent: ethyl acetate Infrared spectroscopic analysis:
- 3250–2500 cm$^{-1}$ υNH$_3$+
- Disappearance of the CN band
- 1605 cm$^{-1}$: υC=C (aromatic)

Proton NMR spectroscopic analysis (300 MHz, DMSO d$_6$ δ):
- 1.14 ppm (triplet, 3H): CH$_3$(a) J$_{a-b}$=7.04 Hz
- 1.67 ppm (multiplet, 6H): CH$_2$(c), CH$_2$(2) and CH$_2$(3)
- 2.63 ppm (multiplet, 7H): CH$_2$(b), CH(d), CH(1) and CH$_2$ (4)
- 6.81–7.11 ppm (multiplet, 3H): aromatic H
- 8.00 ppm (multiplet, 3H): NH$_3$$^+$ Elemental analysis:
- Calculated: C: 70.12% H: 9.25% N: 5.83% Cl: 14.79%
- Found: C: 70.40% H: 8.96% N: 5.83% Cl: 14.69%

PREPARATION 2: 2-(5-ETHYLBENZO[b]THIOPHEN-3-YL)ETHYLAMINE

STAGE A: 4-ETHYLBENZENETHIOL

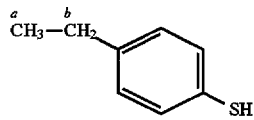

Reactants:
- 4-Ethylbenzenesulfonyl chloride: 0.024 mol (5 g)
- Lithium aluminum hydride: 0.096 mol (3,6 g)
- Anhydrous tetrahydrofuran: 20 cm$^3$ Procedure:

3,6 g of lithium aluminum hydride are added to 20 cm$^3$ of anhydrous tetrahydrofuran with magnetic stirring in a 100 cm$^3$ round-bottomed flask. The mixture is cooled in an ice bath and 5 g of 4-ethylbenzenesulfonyl chloride are then added dropwise. The mixture is stirred for 3 h. The reaction mixture is poured into ice. The aqueous phase is extracted with three volumes of ether. The organic phases are washed with water, dried over magnesium sulfate and then evaporated to dryness. The oil obtained is chromatographed on a column.

Characteristics:
- 138.23 g/mol for C$_8$H$_{10}$S
- Colorless oil
- Rf=0.85 in acetone/toluene/cyclohexane (2/2/1)
- Yield: 70%

Infrared spectroscopic analysis:
- 3080 cm$^{-1}$: υCH aromatic
- 2960–2860 cm$^{-1}$: υCH alkyl
- 2560 cm$^{-1}$: υSH
- 1490 cm$^{-1}$: υC=C aromatic Proton NMR spectroscopic analysis (80 MHz, DMSO-d$_6$ δ):
- 1.25 ppm (triplet, 3H): CH$_3$(a), J$_{a-b}$=7.80 Hz
- 2.65 ppm (quintet, 2H): CH$_2$(b), J$_{b-a}$=7.80 Hz
- 3.40 ppm (singlet, 1H): SH (attenuated in D$_2$O)
- 7.20 ppm (multiplet, 4H): aromatic H

STAGE B: ETHYL 4-ETHYLPHENYLTHIOACETO-ACETATE

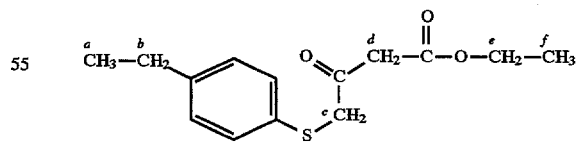

Reactants:
- 4-Ethylbenzenethiol (Stage A): 0.025 mol (3.2 g)
- Ethyl 4-chloroacetoacetate: 0.026 mol (4,2 g)
- Pyridine: 0.1 mol (8 cm$^3$)
- Anhydrous ether: 10 cm$^3$ Procedure:

3.2 g of 4-ethylbenzenethiol and 8 g of pyridine are dissolved in 10 cm$^3$ of anhydrous ether with magnetic stirring in a 100 cm³ round-bottomed flask. 4.2 g of ethyl 4-chloroacetoacetate are added dropwise. The solution is stirred for 2 h at room temperature and then poured into ice. The organic phase is extracted, washed with water, dried over magnesium sulfate and then evaporated to dryness. The oil obtained is purified by column chromatograpy.

Characteristics:
266.22 g/mol for $C_{14}H_{18}O_3S$
Colorless oil
Rf=0.56 in ether/hexane/petroleum ether (2/2/1)
Yield: 50%

Infrared spectroscopic analysis:
2960–2860 cm⁻¹: υCH alkyl
Disappearance of the SH band
1740 cm⁻¹: υCO ester
1710 cm⁻¹: υCO ketone
1490 cm⁻¹: υC=C aromatic Proton NMR spectroscopic analysis (80 MHz, DMSO-$d_6$, δ):
1.20 ppm (multiplet, 6H): $CH_3(a)$ and $CH_3(f)$
2.65 ppm (quintet, 2H): $CH_2(b)$, $J_{b-a}$=7.90 Hz
3.70 ppm (singlet, 2H): $CH_2(c)$
3.75 ppm (singlet, 2H): $CH_2(d)$
4.20 ppm (quintet, 2H): $CH_2(e)$, $J_{e-f}$=7.90 Hz
7.20 ppm (multiplet, 4H): aromatic H STAGE C: ETHYL (5-ETHYLBENZO[b]THIOPHEN-3-YL)ACETATE

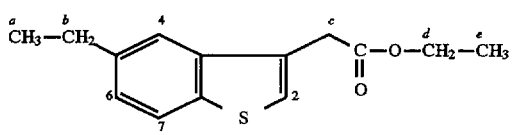

Reactants:
Ethyl 4-ethylphenylthioacetoacetate (Stage B): 0.012 mol (3 g)
Polyphosphoric acid: 30 g
Toluene: 25 cm³
Phosphorus pentoxide: 0.7 g Procedure:
25 cm³ of toluene are added to a 250 cm³ round-bottomed flask containing 30 g of polyphosphoric acid, followed by addition of 0.7 g of phosphorus pentoxide. The ethyl 4-ethylphenylthioacetoacetate is then added in a single portion and the reaction mixture is stirred for 5 h at a temperature of 50° C. The reaction medium is poured into ice. The aqueous phase is extracted with 3 volumes of ether. The organic phases are combined, washed with 3 volumes of water, dried over magnesium sulfate and then evaporated to dryness. The oil obtained is purified by column chromatography.

Characteristics:
248.33 g/mol for $C_{14}H_{16}O_2S$
Colorless oil
Rf=0.74, eluent: ether/hexane/petroleum ether (2/2/1)
Yield: 55%

0 Infrared spectroscopic analysis:
2950–2860 cm⁻¹: υCH alkyl
1730 cm⁻¹: υCO ester
Disappearance of the ketone CO band
1580 cm⁻¹: υC=C aromatic Proton NMR spectroscopic analysis (80 MHz, DMSO-$d_6$, δ):
1.20 ppm (multiplet, 6H): $CH_3(a)$ and $CH_3(e)$
2.75 ppm (quintet, 2H): $CH_2(b)$, $J_{b-a}$=6.95 Hz
3.90 ppm (singlet, 2H): $CH_2(c)$
4.15 ppm (quintet, 2H): $CH_2(d)$, $J_{d-e}$=6.90 Hz
7.20 ppm (doubled doublet 1H): $H_6$, $J_{ortho}$=8.35 Hz, $J_{meta}$=1.40 Hz
7.60 ppm (multiplet, 2H): $H_2$ and $H_4$
7.90 ppm (doublet, 1H): $H_7$, $J_{ortho}$=8.35 Hz Elemental analysis:
Calculated: C: 67.70% H: 6.49% O: 12.88%
Found: C: 67.64% H: 6.54% O: 12.88%

STAGE D: 2-(5-ETHYLBENZO[b]THIOPHEN-3-YL) ACETIC ACID

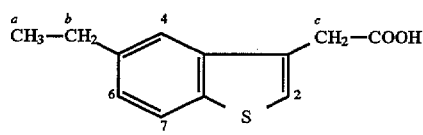

Reactants:
Ethyl (5-ethylbenzo[b]thiophen-3-yl)acetate (Stage C): 0.012 mol (3 g)
Aqueous 20% sodium hydroxide solution: 5 cm³
Methanol: 10 cm³

Procedure:
3 g of ethyl 2-(5-ethylbenzo[b]thiophen-3-yl)acetate are dissolved in 10 cm³ of methanol in a 50 cm³ round-bottomed flask. 5 cm³ of aqueous 20 % sodium hydroxide solution are added. The reaction mixture is stirred at room temperature for 14 h. It is poured into 50 cm³ of water and then extracted with 2 volumes of ether. The aqueous phase is acidified by addition of concentrated hydrochloric acid solution (to pH 3–4). The precipitate which forms is drained and then recrystallized.

Characteristics:
220.28 g/mol for $C_{12}H_{12}O_2S$
White powder
Melting point: 125°–127° C.
Rf=0.74, eluent: ether/hexane/petroleum ether (2/2/1)
Recrystallization solvent: 95° alcohol/water (1/7)
Yield: 50%

Infrared spectroscopic analysis:
3200–2900 cm⁻¹: υOH acid
2960–2840 cm⁻¹: υCH alkyl
1705 cm⁻¹: υCO acid
Disappearance of the ester CO band Proton NMR spectroscopic analysis (300 MHz, DMSO-$d_6$, δ):
1.18 ppm (triplet, 3H): $CH_3(a)$ $J_{a-b}$=7.58 Hz
2.78 ppm (quintet, 2H): $CH_2(b)$ $J_{b-a}$=7.58 Hz
3.89 ppm (singlet, 2H): $CH_2(c)$
7.22 ppm (multiplet, 1 H): $H_6$
7.36 ppm (singlet, 1 H): $H_2$
7.56 ppm (multiplet, 1 H): $H_4$
7.76 ppm (multiplet, 1 H): $H_7$ $J_{ortho}$=8.33 Hz
9.50–10.50 ppm (massive, 1H): COOH Elemental analysis:
Calculated: C: 65.42% H: 5.49% S: 14.56% O: 14.53 %
Found C: 65.32% H: 5.53% S: 14.65% O: 14.50 %

STAGE E: (5-ETHYLBENZO[b]THIOPHEN-3-YL) ACETAMIDE

Reactants:
2-(5-Ethylbenzo[b]thiophen-3-yl)acetic acid (Stage D): 0.006 mol (1.4 g)
Thionyl chloride: 0.024 mol (2.9 g)
Chloroform: 15 cm³

Aqueous 28% ammonia solution: 25 cm³

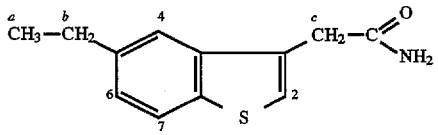

Procedure:

1.4 g of 2-(5-Ethylbenzo[b]thiophen-3-yl)acetic acid are dissolved in 15 cm³ of chloroform with magnetic stirring, in a 100 cm³ flask. 2.86 g of thionyl chloride are added dropwise. The solution is stirred for 3 h at room temperature and then evaporated under vacuum. The residue is taken up in 30 cm³ of ether and then filtered over paper. The flitrate is cooled in an ice bath. 25 cm³ of aqueous 28% ammonia solution are then added in a single portion. The precipitate is drained and then recrystallized.

Characteristics:
219.29 g/mol for $C_{12}H_{13}NOS$
White powder
Melting point: 201°–203° C.
Rf=0.35, eluent: acetone/toluene/cyclohexane (5/3/2)
Recrystallization solvent: hexane
Yield: 65%

Infrared spectroscopic analysis:
3340 and 3160 cm⁻¹: $\upsilon NH_2$ amide
2940–2840 cm⁻¹: $\upsilon CH$ alkyl
Disappearance of the acid CO band
1650 cm⁻¹: $\upsilon CO$ amide Proton NMR spectroscopic analysis (80 MHz, DMSO-d₆, δ):
1.25 ppm (triplet, 3H): $CH_3$(a) $J_{a-b}$=7.40 Hz
2.75 ppm (quintet, 2H): $CH_2$(b) $J_{b-a}$=7.40 Hz
3.60 ppm (singlet, 2H): $CH_2$(c)
7.00 ppm (multiplet, 2H): $NH_2$
7.20 ppm (doubled doublet, 1H): $H_6$ $J_{ortho}$=8.30 Hz $J_{meta}$=1.40 Hz
7.50 ppm (singlet, 1H): $H_2$
7.65 ppm (doublet, 1H): $H_4$ $J_{meta}$=1.40 Hz
7.85 ppm (doublet, 1 H): $H_7 J_{ortho}$=8.30 HZ Elemental analysis:
Calculated: C: 65.72% H: 5.97% N: 6.39%
Found C: 65.91% H: 6.05% N: 6.59%

STAGE F: (5-ETHYLBENZO[b]THIOPHEN-3-YL) ACETONITRILE

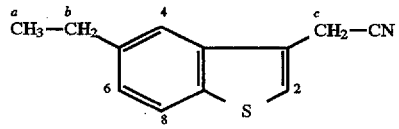

Reactants:
(5-Ethylbenzo[b]thiophen-3-yl)acetamide (Stage E): 0.0011 mol (0.25 g)
Triethylamine: 0.0025 mol (0.25 g)
Trifluoroacetic anhydride: 0.0012 mol (0.27 g)
Anhydrous tetrahydrofuran: 5 cm³

Procedure: 0.25 g of 2-(5-ethylbenzo[b]thiophen-3-yl) acetamide are dissolved in 5 cm³ of anhydrous tetrahydrofuran in a 50 cm³ flask, followed by addition of 0.25 g of triethylamine. The reaction mixture is cooled in an ice-salt bath, and 0.27 g of trifluoroacetic anhydride is added dropwise. The solution is stirred for I h and then evaporated under vacuum. The residue is taken up in water and the precipitate is drained and then recrystallized.

Characteristics:
201.28 g/mol for $C_{12}H_{11}NS$
White powder
Melting point: 59°–60° C.
Rf=0.82, eluent: acetone/toluene/cyclohexane (5/3/2)
Yield: 62%
Recrystallization solvent: 95° alcohol/water (4/1)

Infrared spectroscopic analysis:
Disappearance of the amide $NH_2$ bands
2940–2830 cm⁻¹: $\upsilon CH$ alkyl
2230 cm⁻¹: $\upsilon CN$
Disappearance of the amide CO band Proton NMR spectroscopic analysis (80 MHz, DMSO-d₆, δ):
1.25 ppm (triplet, 3H): $CH_3$(a) $J_{a-b}$=7.50 Hz
2.80 ppm (quintet, 2H): $CH_2$(b) $J_{b-a}$=7.50 Hz
4.25 ppm (singlet, 2H): $CH_2$(c)
7.30 ppm (doubled doublet, 1H): $H_6$ $J_{ortho}$=8.30 hz $J_{meta}$=1.30 Hz
7.70 ppm (multiplet, 2H): $H_2$ and $H_4$
7.95 ppm (doublet, 1H): $H_7$ $J_{ortho}$=8.30 Hz Elemental analysis:
Calculated C: 71.60% H: 5.51% N: 6.96%
Found C: 71.78% H: 5.68% N: 6.99%

STAGE G: 2-(5-ETHYLBENZO[b]THIOPHEN-3-YL) ETHYLAMINE

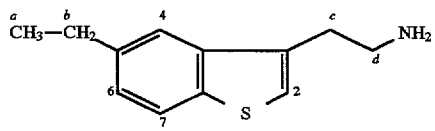

Reactants:
(5-Ethylbenzo[b]thiophen-3-yl)acetonitrile (stage F): 0.004 mol (0.7 g)
Lithium aluminum hydride: 0.01 mol (0.4 g)
Aluminum chloride: 0.01 mol (1.4 g)
Anhydrous ether: 25 cm³

Procedure: 0.4 g of lithium aluminum hydride and 1.4 g of aluminum chloride are added with magnetic stirring to a 100 cm³ flask containing 25 cm³ of anhydrous ether, followed by addition of 0.7 g of (5-ethylbenzo[b] thiophen-3-yl)acetonitrile. After 30 min, the reaction mixture is hydrolyzed on ice and 20 cm³ of aqueous 20% sodium hydroxide solution are added. The ether phase is extracted, washed with 2 volumes of water, dried over magnesium sulfate and then filtered over paper. A stream of hydrogen chloride gas is sparged into the solution and the precipitate formed is drained. The hydrochloride is purified by trituration in cyclohexane.

Characteristics (hydrochloride):
241.77 g/mol for $C_{12}H_{16}ClNS$
White powder
Melting point: 159°–161° C.
Rf=0.15, eluent: acetone/toluene/cyclohexane/ triethylamine (5/3/2/1)
Yield: 50%

Infrared spectroscopic analysis:
3240–2600 cm⁻¹ $\upsilon NH_3^+$
Disappearance of the CN band Proton NMR spectroscopic analysis (80 MHz, CDCl₃, δ):
1.30 ppm (triplet, 3H): $CH_3$(a) $J_{a-b}$=7.50 Hz
2.75 ppm (quintet, 2H): $CH_2$(b) $J_{b-a}$=7.50 Hz
3.15 ppm (multiplet, 4H): $CH_2$(c) and $CH_2$ (d)
7.20 ppm (multiplet, 1H): $H_6$ $J_{ortho}$=8.35 Hz
7.50 ppm (multiplet, 1H): $H_2$
7.70 ppm (multiplet, 1H): $H_4$ 7.95 ppm (doublet, 1H): $H_7$ $J_{ortho}$=8.35 Hz
8.20 ppm (multiplet, 3H): $NH_3^+$ Elemental analysis:
Calculated: C: 59.61% H: 6.67% N: 5.79% Cl: 14.66%
Found: C: 59.78% H: 6.78% N: 5.47% Cl: 14.28%

PREPARATION 3: (R,S) 2-(7-METHYL-1,2,3,4-TETRAHYDRONAPHTH-1-YL)ETHYLAMINE

Working as in Preparation 1, but starting with toluene instead of ethylbenzene, the title compound is obtained.

PREPARATION 4: (R,S) 2-(7-PROPYL-1,2,3,4-TETRAHYDRONAPHTH-1-YL)ETHYLAMINE

Working as in Preparation 1, but replacing the ethylbenzene by propylbenzene, the title compound is obtained.

PREPARATION 5: (R,S) 2-(7-BUTYL-1,2,3,4-TETRAHYDRONAPHTH-1-YL)ETHYLAMINE

Working as in Preparation 1, but replacing the ethylbenzene by butylbenzene, the title compound is obtained.

PREPARATION 6: 2-(5-METHYLINDOL-3-YL) ETHYLAMINE (according to Biosci., Biotechnol., Biochem. 1993, 57 (7), pp 1210–11) PREPARATIONS 7 TO 12:

Working as in Preparation 2, but using the appropriate reactants, the following preparations are obtained:

PREPARATION 7: 2-(5-PROPYLBENZO[b]THIOPHEN-3-YL)ETHYLAMINE

PREPARATION 8: 2-(5-BUTYLBENZO[b]THIOPHEN-3-YL)ETHYLAMINE

PREPARATION 9: 2-(5-HEXYLBENZO[b]THIOPHEN-3-YL)ETHYLAMINE

PREPARATION 10: 2-(5-CYCLOPROPYLBENZO[b]THIOPHEN-3-YL)ETHYLAMINE

PREPARATION 11: 2-(5-CYCLOBUTYLBENZO[b]THIOPHEN-3-YL)ETHYLAMINE

PREPARATION 12: 2-(5-CYCLOPROPYLMETHYLBENZO[b]THIOPHEN-3-YL) ETHYLAMINE

EXAMPLE 1: (R,S) N-[2-(7-ETHYL-1,2,3,4-TETRAHYDRONAPHTH-1-YL)ETHYL]ACETAMIDE

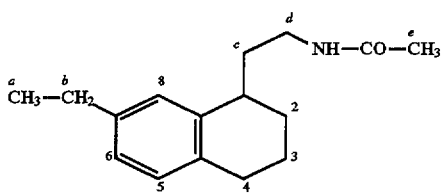

Reactants:
(R,S) 2-(7-Ethyl-1,2,3,4-tetrahydronaphth-1-yl) ethylamine
hydrochloride: 0.008 mol (2 g)
Acetyl chloride: 0.009 mol (0.7 g)
Potassium carbonate: 0.024 mol (1.7 g)
Chloroform: 20 cm³
Water: 10 cm³

The (R,S) 2-(7-ethyl-1,2,3,4-tetrahydronaphth-1-yl) ethylamine hydrochloride from Preparation 1 is dissolved in a water/chloroform mixture (10/20) followed by addition of 3equivalents of potassium carbonate. The mixture is cooled in an ice-salt bath. 1,2 equivalents of acetyl chloride are added dropwise with vigorous magnetic stirring. Stirring is continued for 45 min. The chloroform phase is extracted, washed with 1N hydrochloric acid solution and then with water, dried over magnesium sulfate and evaporated to dryness. The residue obtained is purified by chromatography.

Characteristics:
245.35 g/mol for $C_{16}H_{23}NO$
Colorless oil
Rf=0.43, eluent: acetone/toluene/cyclohexane (5/3/2)
Yield: 62%

Infrared spectroscopic analysis:
3260 cm$^{-1}$: υNH amide
3060 cm$^{-1}$: υCH aromatic
2980–2840 cm$^{-1}$: υCH alkyl
1630 cm$^{-1}$: υCO amide
1540 cm$^{-1}$: υC=C aromatic Proton NMR spectroscopic analysis (300 MHz, DMSO-d$_6$, δ):
1.21 ppm (triplet, 3H): $CH_3$(a), $J_{a-b}$=7.60 Hz
1.80 ppm (multiplet, 6H): $CH_2$(2), $CH_2$(3) and $CH_2$(c)
1.96 ppm (singlet, 3H): $CH_3$(e)
2.58 ppm (quintet, 2H): $CH_2$(b), $J_{b-a}$=7.60 Hz
2.72 ppm (multiplet, 2H): $CH_2$(4)
2.81 ppm (multiplet, 1H): CH (1)
3.37 ppm (multiplet, 2H): $CH_2$(d)
5.63 ppm (multiplet, 1 H): NH amide
6.96 ppm (multiplet, 3H): aromatic H Elemental analysis:
Calculated C: 78.32% H: 9.45% N: 5.71%
Found C: 77.97% H: 9.43% N: 5.59%

EXAMPLE 2: (R,S) N-[2-(7-ETHYL-1,2,3,4-TETRAHYDRONAPHTH-1-YL)ETHYL]BUTYRAMIDE

Working in the same manner as in Example 1, but replacing the acetyl chloride by butyryl chloride, the title compound is obtained.

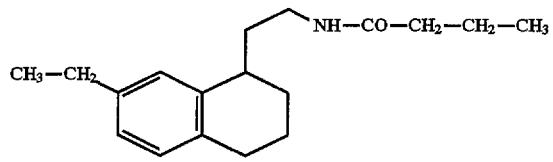

Reactants:
(R,S) 2-(7-Ethyl-1,2,3,4-tetrahydronaphth-1-yl) ethylamine hydrochloride: 0.008 mol (2 g)
Butyryl chloride: 0.009 mol (1 g)
Potassium carbonate: 0.024 mol (3.3 g)
Chloroform: 20 cm³
Water: 10 cm³

Characteristics:
273.40 g/mol for $C_{18}H_{27}NO$
White powder
Melting point: 54°–56° C.
Yield: 75%
Purified by column chromatography in ethyl acetate EXAMPLE 3: (R,S) N-[2-(7-ETHYL-1,2,3,4-TETRAHYDRONAPHTH-1-YL)ETHYL]CYCLOPROPANECARBOXAMIDE

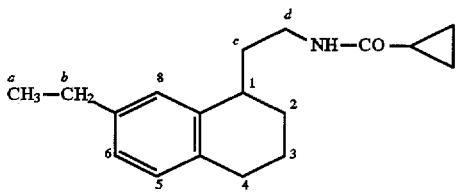

Working in the same manner as in Example 1, but replacing the acetyl chloride by cyclopropanecarboxylic acid chloride, the title compound is obtained.

Reactants:

(R,S) 2-(7-Ethyl-1,2,3,4-tetrahydronaphthalene) ethylamine
  hydrochloride: 0.008 mol (2 g)
  Cyclopropanecarboxylic acid chloride: 0.009 mol (1 g)
  Potassium carbonate: 0.024 mol (3.3 g)
  Chloroform: 20 cm³
  Water: 10 cm³
Characteristics:
  271.39 g/mol for $C_{18}H_{25}NO$
  White powder
  Melting point: 95°–97° C.
  Yield: 80%
  Recrystallization solvent: hexane EXAMPLE 4: (R,S) N-[2-(7-ETHYL-1,2,3,4-TETRAHYDRONAPHTH-1-YL)ETHYL] TRIFLUOROACETAMIDE

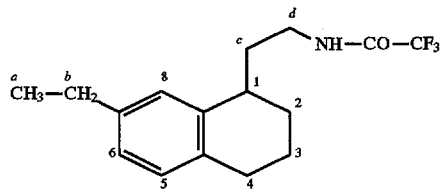

Reactants:

(R,S) 2-(7-Ethyl-1,2,3,4-tetrahydronaphth-1-yl) ethylamine
  hydrochloride: 0.008 mol (2 g)
  Trifluoroacetic anhydride: 0.009 mol (2 g)
  Pyridine: 10 cm³

2 g of (R,S) 2-(7-ethyl-1,2,3,4-tetrahydronaphth-1-yl) ethylamine hydrochloride are dissolved in 10 cm³ of pyridine with magnetic stirring, in a 50 cm³ flask. The reaction mixture is cooled in ice. 2 g of trifluoroacetic anhydride are added dropwise. Stirring is continued for 30 min. The mixture is poured into ice. The aqueous phase is extracted with 3 volumes of ether. The organic phases are combined, washed with 3 volumes of water, dried over magnesium sulfate and then evaporated under vacuum. The residue obtained is purified by column chromatography then recristallized Characteristics:
  299.33 g/mol for $C_{16}H_{20}F_3NO$
  White powder
  Melting point: 66°–69° C.
  Yield: 60%
  Purified by column chromatography (eluent: ethyl acetate)
  Recristallisation solvent: hexan Infrared spectroscopic analysis:
  3280 cm⁻¹: υNH amide
  3070 cm⁻¹: υC—H aromatic
  2960–2840 cm⁻¹: υC—H alkyl
  1630 cm⁻¹: υC=O amide
  1550 cm⁻¹: υC=C aromatic NMR spectroscopic analysis (300 MHz, $CDCl_3$, δ):
  1.21 ppm (triplet, 3H): $CH_3(a)$ $J_{a-b}$=7.59 Hz
  1.85 ppm (multiplet, 6H): $CH_2(c)$, $CH_2(2)$ and $CH_2(3)$,
  2.58 ppm (quintet, 2H): $CH_2(b)$ $J_{b-a}$=7.59 Hz
  2.73 ppm (multiplet, 2H): $CH_2(4)$
  2.84 ppm (multiplet, 1H): CH (1)
  3.74 ppm (multiplet, 2H): $CH_2(d)$
  6.52 ppm (multiplet, 1H):NH
  6.97 ppm (multiplet, 3H): aromatic H Elemental analysis:
  Calculated C: 64.20% H: 6.74% N: 4.68% F: 19.04%
  Found : C: 64.13% H: 6.70% N: 4.62% F: 18.78%

EXAMPLE 5: (R,S) N-[2-(7-ETHYL-1,2,3,4-TETRAHYDRONAPHTH-1-YL)ETHYL] VALERAMIDE

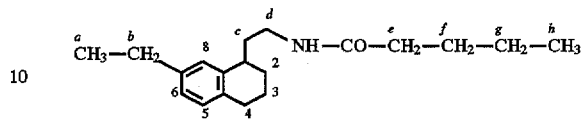

Working in the same manner as in Example 1, but replacing the acetyl chloride by valeryl chloride, the title compound is obtained.

Reactants:

(R,S) 2-(7-Ethyl-1,2,3,4-tetrahydronaphth-1-yl) ethylamine
  hydrochloride: 0.008 mol (2 g)
  Valeryl chloride: 0.009 mol (1.1 g)
  Potassium carbonate: 0.024 mol (3.3 g)
  Chloroform: 20 cm³
  Water: 10 cm³

Characteristics:
  287.43 g/mol for $C_{18}H_{29}NO$
  Colorless oil
  Yield: 65%
  Purified by column chromatography in ethyl acetate Infrared spectroscopic analysis:
  3290 cm⁻¹: υNH amide
  2990–2820 cm⁻¹: υC—H alkyl
  1630 cm⁻¹: υC=O amide
  1530 cm⁻¹: υC=C aromatic NMR spectroscopic analysis (300 MHz, $CDCl_3$, δ)
  0.91 ppm (triplet, 3H): $CH_3(h)$, $J_{h-g}$=7.29 Hz
  1.21 ppm (triplet, 3H): $CH_3(a)$, $J_{a-b}$=7.59 Hz
  1.33 ppm (multiplet, 2H): $CH_2(g)$
  1.75 ppm (multiplet, 8H): $CH_2(2)$, $CH_2(3)$, $CH_2(c)$, $CH_2(f)$
  2.15 ppm (triplet, 2H): $CH_2(e)$, $J_{e-f}$=7.57 Hz
  2.58 ppm (quintet, 2H): $CH_2(b)$, $J_{b-a}$=7.59 Hz
  2.71 ppm (multiplet, 2H): $CH_2(4)$
  2.80 ppm (multiplet, 1 H): CH (1)
  3.37 ppm (multiplet, 2H): $CH_2(d)$
  5.71 ppm (multiplet, 1H): NH
  6.97 ppm (multiplet, 3H): aromatic H

EXAMPLES 6 TO 12

Working in the same manner as in Example 1, but using the appropriate acyl chloride or iso(thio)cyanate, the following examples are obtained:

EXAMPLE 6: (R,S) N-[2-(7-ETHYL-1,2,3,4-TETRAHYDRONAPHTH-1-YL)ETHYL] CYCLOBUTYLCARBOXAMIDE

EXAMPLE 7: (R,S) N-[2-(7-ETHYL-1,2,3,4-TETRAHYDRONAPHTH-1-YL)ETHYL]-PROPIONAMIDE

EXAMPLE 8: (R,S) N-[2-(7-ETHYL-1,2,3,4-TETRAHYDRONAPHTH-1-YL)ETHYL]-ISOBUTYRAMIDE

EXAMPLE 9: (R,S) N-[2-(7-ETHYL-1,2,3,4-TETRAHYDRONAPHTH-1-YL)ETHYL]-N'-METHYLUREA

EXAMPLE 10: (R,S) N-[2-(7-ETHYL-1,2,3,4-TETRAHYDRONAPHTH-1-YL)ETHYL]-N'-PROPYLUREA

EXAMPLE 11: (R,S) N-[2-(7-ETHYL-1,2,3,4-TETRAHYDRONAPHTH-1-YL)ETHYL]-N'-CYCLOPROPYLUREA

EXAMPLE 12: (R,S) N-[2-(7-ETHYL-1,2,3,4-TETRAHYDRONAPHTH-1-YL)ETHYL]-N'-CYCLOBUTYLUREA

EXAMPLE 13: (R,S) N-[2-(5-ETHYLBENZOTHIOPHEN-3-YL)ETHYL] CYCLOBUTANECARBOXAMIDE

Working in the same manner as for the amidation reaction of Example 1, but replacing the 2-(7-ethyl-1,2,3,4-tetrahydronaphth-1-yl)ethylamine by 2-(5-ethylbenzo[b]thiophen-3-yl)ethylamine (Preparation 2) and the acetyl chloride by cyclobutanecarboxylic acid chloride, the title compound is obtained.

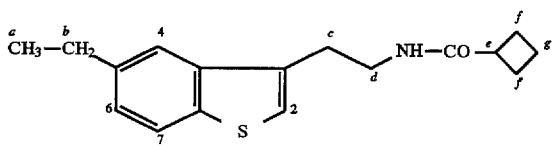

Reactants:
2-(5-Ethylbenzo[b]thiophen-3-yl)ethylamine hydrochloride: 0.001 mol (0.25 g)
Potassium carbonate: 0.003 mol (0.4 g)
Cyclobutanecarboxylic acid chloride: 0.0013 mol (0.16 g)
Chloroform: 16 cm$^3$
Water: 8 cm$^3$ Characteristics:
286.40 g/mol for $C_{17}H_{20}NOS$
White powder
Melting point: 105°–107° C.
Rf=0.70, eluent: acetone/toluene/cyclohexane (5/3/2)
Recrystallization solvent: hexane
Yield: 70%

Infrared spectroscopic analysis:
3275 cm$^{-1}$: υNH amide
3070 cm$^{-1}$: υCH aromatic
2980–2840 cm$^{-1}$: υCH alkyl
1630 cm$^{-1}$: υCO amide
1550 cm$^{-1}$: υC=C aromatic Proton NMR spectroscopic analysis (300 MHz, DMSO-d$_6$, δ):
1.25 ppm (triplet, 3H): $CH_3$(a) $J_{a-b}$=7.53 Hz
1.97 ppm (multiplet, 6H): $CH_2$(f), $CH_2$(f) and $CH_2$(g)
2.57 ppm (quintet, 2H): $CH_2$(b) $J_{b-a}$=7.53 Hz
2.95 ppm (multiplet, 3H): $CH_2$(c)
3.36 ppm (multiplet, 2H): $CH_2$(d)
7.25 ppm (multiplet, 1H): $H_6 J_{ortho}$=8.27 HZ
7.40 ppm (singlet, 1H): $H_2$
7.68 ppm (multiplet, 1H): $H_{4l}$
7.85 ppm (multiplet, 2H): $H_7$ and NH Elemental analysis:
Calculated: C: 71.29% H: 7.04% N: 4.89% Cl: 11.20%
Found: C: 70.88% H: 7.32% N: 4.90% Cl: 11.02%

EXAMPLE 14: N-[2-(5-ETHYLBENZOTHIOPHEN-3-YL)ETHYL]ACETAMIDE

Working in the same manner as for the synthesis of the compound of Example 14, but replacing the cyclobutanecarboxylic acid chloride by acetyl chloride, the title compound is obtained.

Characteristics:
247.36 g/mol for $C_{14}H_{17}NOS$
Melting point: 87°–88° C.

EXAMPLES 15 TO 24

Starting with N-[2-(5-ethylbenzothiophen-3-yl)] ethylamine, but using the appropriate acid chloride or isocyanate, the following examples are obtained:

EXAMPLE 15: N-[2-(5-ETHYLBENZOTHIOPHEN-3-YL)ETHYL]BUTYRAMIDE
Melting point: 62°–64° C.

EXAMPLE 16: N-[2-(5-ETHYLBENZOTHIOPHEN-3-YL)ETHYL]PROPIONAMIDE
Melting point: 92°–93° C.

EXAMPLE 17: N-[2-(5-ETHYLBENZOTHIOPHEN-3-YL)ETHYL]VALERAMIDE
Melting point: 61°–63° C.

EXAMPLE 18: N-[2-(5-ETHYLBENZOTHIOPHEN-3-YL)ETHYL]CYCLOPROPANECARBOXAMIDE
Melting point: 92°–94° C.

EXAMPLE 19: N-[2-(5-ETHYLBENZOTHIOPHEN-3-YL)ETHYL]CYCLOHEXANECARBOXAMIDE

EXAMPLE 20: N-[2-(5-ETHYLBENZOTHIOPHEN-3-YL)ETHYL]-N'-PROPYLUREA
Melting point: 137°–139° C.

EXAMPLE 21: N-[2-(5-ETHYLBENZOTHIOPHEN-3-YL)ETHYL]-N'-METHYLUREA
Melting point: 133°–135° C.

EXAMPLE 22: N-[2-(5-ETHYLBENZOTHIOPHEN-3-YL)ETHYL]-N'-ETHYLUREA

EXAMPLE 23: N-[2-(5-ETHYLBENZOTHIOPHEN-3-YL)ETHYL]-N'-CYCLOPROPYLUREA

EXAMPLE 24: N-[2-(5-ETHYLBENZOTHIOPHEN-3-YL)ETHYL]-N'-CYCLOHEXYLUREA

EXAMPLE 25: N-[2-(5-ETHYLBENZOTHIOPHEN-3-YL)ETHYL]TRIFLUOROACETAMIDE

EXAMPLE 26: N-[2-(5-METHYLINDOL-3-YL)ETHYL] ACETAMIDE

Working in the same manner as for the amidation reaction of Example 1, but using 5-methyltryptamine (Preparation 6) and acetyl chloride as reactants, the title compound is obtained.

EXAMPLES 27 TO 31

Starting with 5-methyltryptamine, but using the appropriate acyl chloride or isocyanate, the following examples are obtained:

EXAMPLE 27: N-[2-(5-METHYLINDOL-3-YL)ETHYL] CYCLOPROPANECARBOXAMIDE

EXAMPLE 28: N-[2-(5-METHYLINDOL-3-YL)ETHYL] BUTYRAMIDE

EXAMPLE 29: N-[2-(5-METHYLINDOL-3-YL)ETHYL] TRIFLUOROACETAMIDE

EXAMPLE 30: N-[2-(5-METHYLINDOL-3-YL)ETHYL]-N'-METHYLUREA

EXAMPLE 31: N-[2-(5-METHYLINDOL-3-YL)ETHYL]-N'-PROPYLUREA

EXAMPLE 32: (R,S) N-[2-(7-METHYL-1,2,3,4-TETRAHYDRONAPHTH-1-YL)ETHYL]-ACETAMIDE

Working in the same manner as for the reaction for the amidation of the compound of Example 1, but using 2-(7-methyl-1,2,3,4-tetrahydronaphth-1-yl)ethylamine (Preparation 3) and acetyl chloride as reactants, the title compound is obtained.

EXAMPLES 33 TO 36

Starting with (R,S) 2-(7-methyl-1,2,3,4-tetrahydronaphth-1-yl)ethylamine, but using the appropriate acyl chloride or isocyanate, the following examples are obtained:

EXAMPLE 33: (R,S) N-[2-(7-METHYL-1,2,3,4-TETRAHYDRONAPHTH-1-YL)ETHYL]CYCLOPROPANECARBOXAMIDE

EXAMPLE 34: (R,S) N-[2-(7-METHYL-1,2,3,4-TETRAHYDRONAPHTH-1-YL)ETHYL]-N'-METHYLUREA

EXAMPLE 35: (R,S) N-[2-(7-METHYL-1,2,3,4-TETRAHYDRONAPHTH-1-YL)ETHYL]-N'-PROPYLUREA

EXAMPLE 36: (R,S) N-[2-(7-METHYL-1,2,3,4-TETRAHYDRONAPHTH-1-YL)ETHYL]-BUTYRAMIDE

EXAMPLE 37: (R,S) N-[2-(7-PROPYL-1,2,3,4-TETRAHYDRONAPHTH-1-YL)ETHYL]-ACETAMIDE

Working in the same manner as in the reaction for the amidation of the compound of Example 1, but using (R,S) 2-(7-propyl-1,2,3,4-terahydronaphth-1-yl)ethylamine (Preparation 4) as reactant, the title compound is obtained.

EXAMPLES 38 TO 41

Starting with (R,S) 2-(7-propyl-1,2,3,4-tetrahydronaphth-1-yl)ethylamine, but using the appropriate acid chloride or isocyanate, the following examples are obtained:

EXAMPLE 38: (R,S) N-[2-(7-PROPYL-1,2,3,4-TETRAHYDRONAPHTH-1-YL)ETHYL]CYCLOPROPANECARBOXAMIDE

EXAMPLE 39: (R,S) N-[2-(7-PROPYL-1,2,3,4-TETRAHYDRONAPHTH-1-YL)ETHYL]-N'-METHYLUREA

EXAMPLE 40: (R,S) N-[2-(7-PROPYL-1,2,3,4-TETRAHYDRONAPHTH-1-YL)ETHYL]-N'-PROPYLUREA

EXAMPLE 41: (R,S) N-[2-(7-PROPYL-1,2,3,4-TETRAHYDRONAPHTH-1-YL)ETHYL]-TRIFLUOROACETAMIDE

EXAMPLE 42: (R,S) N-[2-(7-BUTYL-1,2,3,4-TETRAHYDRONAPHTH-1-YL)ETHYL]-ACETAMIDE

Working in the same manner as for the reaction for the amidation of the compound of Example 1, but using 2-(7-butylnaphth-1-yl)ethylamine (Preparation 5) as reactant, the title compound is obtained.

EXAMPLES 43 TO 46

Starting with 2-(7-butyl-1,2,3,4-tetrahydronaphth-1-yl) ethylamine, but using the appropriate acid chloride or isocyanate, the following examples are obtained:

EXAMPLE 43: (R,S) N-[2-(7-BUTYL-1,2,3,4-TETRAHYDRONAPHTH-1-YL)ETHYL]-N'-METHYLUREA

EXAMPLE 44: (R,S) N-[2-(7-BUTYL-1,2,3,4-TETRAHYDRONAPHTH-1-YL)ETHYL]-N'-PROPYLUREA

EXAMPLE 45: (R,S) N-[2-(7-BUTYL-1,2,3,4-TETRAHYDRONAPHTH-1-YL)ETHYL]CYCLOPROPANECARBOXAMIDE

EXAMPLE 46: (R,S) N-[2-(7-BUTYL-1,2,3,4-TETRAHYDRONAPHTH-1-YL)ETHYL]-TRIFLUOROACETAMIDE

EXAMPLES 47 TO 52

Using Preparations 1 and 2, but employing the appropriate isothiocyanates, the compounds of the following examples are obtained:

EXAMPLE 47: (R,S) N-[2-(7-ETHYL-1,2,3,4-TETRAHYDRONAPHTH-1-YL)ETHYL]-N'-METHYLTHIOUREA

EXAMPLE 48: (R,S) N-[2-(7-ETHYL-1,2,3,4-TETRAHYDRONAPHTH-1-YL)ETHYL]-N'-ETHYLTHIOUREA

EXAMPLE 49: (R,S) N-[2-(7-ETHYL-1,2,3,4-TETRAHYDRONAPHTH-1-YL)ETHYL]-N'-PROPYLTHIOUREA

EXAMPLE 50: N-[2-(5-ETHYLBENZOTHIOPHEN-3-YL)ETHYL]-N'-METHYLTHIOUREA

EXAMPLE 51: N-[2-(5-ETHYLBENZOTHIOPHEN-3-YL)ETHYL]-N'-ETHYLTHIOUREA

EXAMPLE 52: N-[2-(5-ETHYLBENZOTHIOPHEN-3-YL)ETHYL]-N'-PROPYLTHIOUREA

EXAMPLES 53 TO 100

Working as described above, but starting with Preparations 7 to 12, the compounds of the following examples are obtained:

EXAMPLE 53: N-[2-(5-PROPYLBENZOTHIOPHEN-3-YL)ETHYL]ACETAMIDE

EXAMPLE 54: N-[2-(5-PROPYLBENZOTHIOPHEN-3-YL)ETHYL]PROPIONAMIDE

EXAMPLE 55: N-[2-(5-PROPYLBENZOTHIOPHEN-3-YL)ETHYL]BUTYRAMIDE

EXAMPLE 56: N-[2-(5-PROPYLBENZOTHIOPHEN-3-YL)ETHYL]VALERAMIDE

EXAMPLE 57: N-[2-(5-PROPYLBENZOTHIOPHEN-3-YL)ETHYL]CYCLOPROPANECARBOXAMIDE

EXAMPLE 58: N-[2-(5-PROPYLBENZOTHIOPHEN-3-YL)ETHYL]CYCLOBUTANECARBOXAMIDE

EXAMPLE 59: N-[2-(5-PROPYLBENZOTHIOPHEN-3-YL)ETHYL]-N'-METHYLUREA

EXAMPLE 60: N-[2-(5-PROPYLBENZOTHIOPHEN-3-YL)ETHYL]-N'-PROPYLUREA

EXAMPLE 61: N-[2-(5-BUTYL-BENZOTHIOPHEN-3-YL)ETHYL]ACETAMIDE

EXAMPLE 62: N-[2-(5-BUTYLBENZOTHIOPHEN-3-YL)ETHYL]PROPIONAMIDE

EXAMPLE 63: N-[2-(5-BUTYLBENZOTHIOPHEN-3-YL)ETHYL]BUTYRAMIDE

EXAMPLE 64: N-[2-(5-BUTYLBENZOTHIOPHEN-3-YL)ETHYL]VALERAMIDE

EXAMPLE 65: N-[2-(5-BUTYLBENZOTHIOPHEN-3-YL)ETHYL]CYCLOPROPANECARBOXAMIDE

EXAMPLE 66: N-[2-(5-BUTYLBENZOTHIOPHEN-3-YL)ETHYL]CYCLOBUTANECARBOXAMIDE

EXAMPLE 67: N-[2-(5-BUTYLBENZOTHIOPHEN-3-YL)ETHYL]-N'-METHYLUREA

EXAMPLE 68: N-[2-(5-BUTYLBENZOTHIOPHEN-3-YL)ETHYL]-N'-PROPYLUREA

EXAMPLE 69: N-[2-(5-HEXYLBENZOTHIOPHEN-3-YL)ETHYL]ACETAMIDE

EXAMPLE 70: N-[2-(5-HEXYLBENZOTHIOPHEN-3-YL)ETHYL]PROPIONAMIDE

EXAMPLE 71: N-[2-(5-HEXYLBENZOTHIOPHEN-3-YL)ETHYL]BUTYRAMIDE

EXAMPLE 72: N-[2-(5-HEXYLBENZOTHIOPHEN-3-YL)ETHYL]VALERAMIDE

EXAMPLE 73: N-[2-(5-HEXYLBENZOTHIOPHEN-3-YL)ETHYL]CYCLOPROPANECARBOXAMIDE

EXAMPLE 74: N-[2-(5-HEXYLBENZOTHIOPHEN-3-YL)ETHYL]CYCLOBUTANECARBOXAMIDE

EXAMPLE 75: N-[2-(5-HEXYLBENZOTHIOPHEN-3-YL)ETHYL]-N'-METHYLUREA

EXAMPLE 76: N-[2-(5-HEXYLBENZOTHIOPHEN-3-YL)ETHYL]-N'-PROPYLUREA

EXAMPLE 77: N-[2-(5-CYCLOPROPYLBENZOTHIOPHEN-3-YL) ETHYL]ACETAMIDE

EXAMPLE 78: N-[2-(5-CYCLOPROPYLBENZOTHIOPHEN-3-YL)ETHYL]PROPIONAMIDE

EXAMPLE 79: N-[2-(5-CYCLOPROPYLBENZOTHIOPHEN-3-YL)ETHYL]BUTYRAMIDE

EXAMPLE 80: N-[2-(5-CYCLOPROPYLBENZOTHIOPHEN-3-YL)ETHYL]VALERAMIDE

EXAMPLE 81: N-[2-(5-CYCLOPROPYLBENZO-THIOPHEN-3-YL)ETHYL]CYCLOPROPANECARBOXAMIDE

EXAMPLE 82: N-[2-(5-CYCLOPROPYLBENZO-THIOPHEN-3-YL)ETHYL]CYCLOBUTANECARBOXAMIDE

EXAMPLE 83: N-[2-(5-CYCLOPROPYLBENZO-THIOPHEN-3-YL)ETHYL]-N'-METHYLUREA

EXAMPLE 84: N-[2-(5-CYCLOPROPYLBENZO-THIOPHEN-3-YL)ETHYL]-N'-PROPYLUREA

EXAMPLE 85: N-[2-(5-CYCLOBUTYLBENZO-THIOPHEN-3-YL)ETHYL]ACETAMIDE

EXAMPLE 86: N-[2-(5-CYCLOBUTYLBENZO-THIOPHEN-3-YL)ETHYL]PROPIONAMIDE

EXAMPLE 87: N-[2-(5-CYCLOBUTYLBENZO-THIOPHEN-3-YL)ETHYL]BUTYRAMIDE

EXAMPLE 88: N-[2-(5-CYCLOBUTYLBENZO-THIOPHEN-3-YL)ETHYL]VALERAMIDE

EXAMPLE 89: N-[2-(5-CYCLOBUTYLBENZO-THIOPHEN-3-YL)ETHYL]CYCLO-PROPANECARBOXAMIDE

EXAMPLE 90: N-[2-(5-CYCLOBUTYLBENZO-THIOPHEN-3-YL)ETHYL]CYCLO-BUTANECARBOXAMIDE

EXAMPLE 91: N-[2-(5-CYCLOBUTYLBENZO-THIOPHEN-3-YL)ETHYL]-N'-METHYLUREA

EXAMPLE 92: N-[2-(5-CYCLOBUTYLBENZO-THIOPHEN-3-YL) ETHYL]-N'-PROPYLUREA

EXAMPLE 93: N-[2-(S-CYCLOPROPYLMETHYL-BENZOTHIOPHEN-3-YL)ETHYL]-ACETAMIDE

EXAMPLE 94: N-[2-(5-CYCLOPROPYLMETHYL-BENZOTHIOPHEN-3-YL)ETHYL]-PROPIONAMIDE

EXAMPLE 95: N-[2-(5-CYCLOPROPYLMETHYL-BENZOTHIOPHEN-3-YL)ETHYL]-BUTYRAMIDE

EXAMPLE 96: N-[2-(5-CYCLOPROPYLMETHYL-BENZOTHIOPHEN-3-YL)ETHYL]-VALERAMIDE

EXAMPLE 97: N-[2-(5-CYCLOPROPYLMETHYL-BENZOTHIOPHEN-3-YL)ETHYL]-CYCLOPROPANECARBOXAMIDE

EXAMPLE 98: N-[2-(5-CYCLOPROPYLMETHYL-BENZOTHIOPHEN-3-YL)ETHYL]-CYCLOBUTANECARBOXAMIDE

EXAMPLE 99: N-[2-(5-CYCLOPROPYLMETHYL-BENZOTHIOPHEN-3-YL)ETHYL]-N'-METHYLUREA

EXAMPLE 100: N-[2-(5-CYCLOPROPYLMETHYL-BENZOTHIOPHEN-3-YL)ETHYL]-N'-PROPYLUREA

EXAMPLE 101: N-[2-(7-ETHYLNAPHT-1-YL)ETHYL] ACETAMIDE

EXAMPLE 102: N-[2-(7-ETHYLNAPHT-1-YL)ETHYL] CYCLOPROPANECARBOXAMIDE

EXAMPLE 103: N-[2-(7-ETHYLNAPHT-1-YL)ETHYL] CYCLOBUTANECARBOXAMIDE

EXAMPLE 104: N-[2-(7-ETHYLNAPHT-1-YL)ETHYL] TRIFLUOROACETAMIDE

EXAMPLE 105: N-[2-(7-ETHYLNAPHT-1-YL)ETHYL] N'-METHYLUREE

EXAMPLE 106: N-[2-(7-ETHYLNAPHT-1-YL)ETHYL] N'-PROPYLUREE

EXAMPLE 107: N-[2-(7-METHYLNAPHT-1-YL) ETHYL]ACETAMIDE

EXAMPLE 108: N-[2-(7-PROPYLNAPHT-1-YL)ETHYL] ACETAMIDE

EXAMPLE 109: N-[2-(7-BUTYLNAPHT-1-YL)ETHYL] ACETAMIDE

EXAMPLE 110: N-[2-(7-HEXYLNAPHT-1-YL)ETHYL] ACETAMIDE

PHARMACOLOGICAL STUDY

EXAMPLE A: STUDY OF THE ACUTE TOXICITY

The acute toxicity was evaluated after oral administration to batches of 8 mice (26±2 grams). The animals were observed at regular intervals on the first day and daily for the two weeks following the treatment. The $LD_{50}$, leading to the death of 50% of the animals, was evaluated.

The $LD_{50}$ of the test products is greater than 1000 mg $kg^{-1}$ for the test compounds which indicates the low toxicity of the compounds of the invention.

EXAMPLE B: STUDY OF THE BINDING TO THE MELATONIN RECEPTORS

B1) STUDY ON SHEEP PARS TUBERALIS CELLS

The studies of the binding of the compounds of the invention to the melatonin receptors were performed according to the standard techniques, on sheep pars tuberalis cells. The pars tuberalis of the adenohypophysis is indeed characterized in mammals, by a high density of melatonin receptors (Journal of Neuroendocrinology vol. (1), pp 1–4 (1989)).

PROCEDURE

1) Sheep pars tuberalis membranes are prepared and used as target tissue in saturation experiments in order to determine the binding capacities and affinities for 2-[$^{125}$I]-iodomelatonin.

2) The sheep pars tuberalis membranes are used as target tissue, with various test compounds, in competitive binding experiments relative to 2-[$^{125}$I]-melatonin.

Each experiment is performed in triplicate and a range of different concentrations is tested for each compound.

The results make it possible to determine, after statistical treatment, the binding affinities of the test compound.

RESULTS

It is seen that the compounds of the invention possess a powerful affinity for the melatonin receptors, this affinity being stronger than that for melatonin itself.

B2) STUDY ON CHICK (*GALLUS DOMESTICUS*) BRAIN CELL MEMBRANES

The animals used are 12-day old chicks (*Gallus domesticus*). They are sacrificed between 13.00 h and 17.00 h on the day of their arrival. The brains are rapidly removed and frozen at −200° C. and then stored at −80° C. The membranes are prepared according to the method described by Yuan and Pang (Journal of Endocrinology 128, pages 475–482, 1991 ). 2-[$^{125}$I]-melatonin is incubated in the presence of the membranes in a solution buffered to pH 7.4 for 60 min at 25° C. After this period, the membrane suspension is filtered (Whatman GF/C). The radioactivity retained on the filter is determined using a Beckman® LS 6000 liquid scintillation counter.

The products used are:
2-[$^{125}$I]-melatonin
melatonin
common products
original molecules In primary screening, the molecules are tested at 2 concentrations ($10^{-7}$ and $10^{-5}$M). Each result is the average of n=3 independent measurements. The active molecules retained according to the results of the primary screening formed the subject of a quantitative determination of their efficacy ($IC_{50}$). They are used at 10 different concentrations.

Thus, the $IC_{50}$ values found for the preferred compounds of the invention, which correspond to the values of the affinity, show that the binding of the tested compounds of the invention is very powerful.

EXAMPLE C: FOUR-PLATE TEST

The products of the invention are administered esophageally to batches of ten mice. One batch receives gum syrup. 30 minutes after administration of the products to be studied, the animals are placed in chambers the floor of which comprises four metal plates. Each time the animal passes from one plate to another, it receives a mild electric discharge (0.35 mA). The number of passages is recorded for one minute. After administration, the compounds of the invention significantly increase the number of passages, which shows the anxiolytic activity of the compounds of the invention.

EXAMPLE D: COMPOUNDS OF THE INVENTION ON THE CIRCADIAN RHYTHMS OF RAT LOCOMOTOR ACTIVITY

The involvement of melatonin in driving, via the alternating day/night cycle, most of the physiological, biochemical and behavioral circadian rhythms has made it possible to establish a pharmacological model for the search for melatoninergic ligands.

The effects of the molecules are tested on a number of parameters and in particular on the circadian rhythms of locomotor activity, which represent a reliable marker of the activity of the endogenous circadian clock.

In this study, the effects of such molecules on a particular experimental model, namely a rat placed in temporal isolation (permanent darkness), is evaluated.

EXPERIMENTAL PROCEDURE

On their arrival at the laboratory, one-month-old male Long Evans rats are subjected to a lighting cycle of 12 h of light per 24 h (12:12 LD).

After 2 to 3 weeks of adaptation, they are placed in cages equipped with a wheel connected to a recording system so as to detect the phases of locomotor activity and thus to monitor the nyctohemeral (LD) or circadian (DD) rhythms.

As soon as the rhythms recorded show evidence of a stable driving pattern for the 12:12 LD lighting cycle, the rats are placed in permanent darkness (DD).

Two to three weeks later, when the free, non-driven pattern (rhythm reflecting that of the endogenous clock) is clearly established, the rats receive a daily administration of the test molecule.

The observations are made by virtue of the visualization of the rhythms of activity:

rhythms of activity driven by the lighting rhythm, disappearance of the driving pattern for the rhythms in permanent darkness, rhythms driven by the daily administration of the molecule; transient or long-lasting effect.

A software program makes it possible:

to measure the duration and intensity of the activity, the period of the rhythm in the animals under free, non-driven conditions and during the treatment, possibly to demonstrate, by spectral analysis, the existence of circadian and non-circadian components (for example ultradian components).

RESULTS:

It is clearly seen that the compounds of the invention make it possible to have a powerful effect on the circadian rhythm via the melatoninergic system.

EXAMPLE E: ANTIARRYTHMIC ACTIVITY
PROCEDURE (Ref: LAWSON J. W. et al. J. Pharmacol. Expert. Therap. 160: 22–31, 1968)

The test substance is administered intrapedtoneally to a group of 3 mice 30 min before exposure to anesthesia by chloroform. The animals are then observed for 15 min. The absence of recording of arrythmia and of cardiac frequencies above 200 beats/min (control: 400–480 beats/min) in at least two animals indicates a significant protection.

EXAMPLE F: PLATELET ANTI-AGGREGATING ACTIVITY
PROCEDURE (Ref.: Bertele V. et al. Science. 220: 517–519, 1983 Ibid, Eur. J. Pharmacol. 85: 331–333, 1982)

The compounds of the invention (100 µg/ml) are tested for their capacity to inhibit irreversible platelet aggregation induced by sodium arachidonate (50 µg/ml) in platelet-enriched rabbit plasma.

An inhibition of more than 50% in the maximum aggregation indicates a significant activity for the compounds of the invention.

This in vitro test shows that the compounds of the invention are good candidates for the treatment of cardiovascular diseases, in particular thrombosis.

EXAMPLE G: PROLONGATION OF THE BLEEDING TIME
PROCEDURE (Ref.: Djana E. et al. Thrombosis Research. 15: 191–197, 1979) Butler K. D. et al. Thromb. Haemostasis. 47: 46–49, 1982)

The test compounds are administered orally (100 mg/kg) to a group of 5 mice 1 h before the standardized sectioning of the end of each tail (0.5 mm).

The mice are immediately suspended vertically, the tails being immersed to a depth of 2 cm in a test tube containing isotonic saline solution at 37° C.

The time required for the bleeding to stop for a period of 15 seconds is then determined.

A prolongation of more than 50% in the bleeding time relative to a control group of animals is considered as being significant for the compounds of the invention.

This in vivo test confirms the advantage of the compounds of the invention for the treatment of cardiovascular pathologies, since the compounds of the invention prolong the bleeding time.

EXAMPLE H: TEST OF HYPOBARIC HYPOXIA

PROCEDURE (Ref.: Gotti B., and Depoortere H., Circ. Cerebrale, Congress on Cerebral Circulation, Toulouse, 105–107, 1979)

The test compounds are administered intraperitoneally (100 mg/kg) to a group of 3 mice 30 minutes before they are placed in a chamber at a hypobaric pressure of 20 cm Hg.

The prolongation of the survival time, relative to a group of animals treated with the vehicle, by more than 100% in the absence of a depressant effect on the central nervous system indicates a cerebroprotective activity of the compounds of the invention.

EXAMPLE I: PHARMACEUTICAL COMPOSITION: TABLETS 1000 tablets containing a 5 mg dose of N-[2-(5-ethylbenzothiophen-3-yl)ethyl]acetamide

| | |
|---|---|
| N-[2-(5-Ethylbenzothiophen-3-yl)ethyl]acetamide | 5 g |
| Wheat starch | 20 g |
| Corn starch | 20 g |
| Lactose | 30 g |
| Magnesium stearate | 2 g |
| Silica | 1 g |
| Hydroxypropyl cellulose | 2 g |

We claim:
1. A compound selected from those of formula (I):

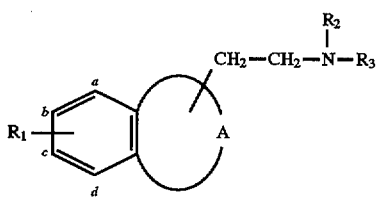

in which:
R₁ represents a group chosen from alkyl, substituted alkyl, cycloalkyl, substituted cycloalkyl, cycloalkylalkyl, and substituted cycloalkylalkyl, A forms, with the benzene ring to which it is attached, a cyclic group chosen from benzothiophene and, 2,3-dihydrobenzothiophene, R² represents hydrogen or alkyl,
R₃ represents:
a group R₃₁:

with X representing sulfur or oxygen and R₄ representing hydrogen or a group R₄₁ chosen from alkyl, substituted alkyl, alkenyl, alkynyl, cycloalkyl, substituted cycloalkyl, cycloalkylalkyl, and substituted cycloalkylalkyl,
or a group of formula (R₃₂):

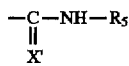

with X' representing sulfur or oxygen and R₅ representing hydrogen or a group chosen from alkyl, substituted alkyl, cycloalkyl, substituted cycloalkyl, cycloalkylalkyl, and substituted cycloalkylalkyl, it being understood that in the description of formula (I), and except where otherwise mentioned:
the terms "alkyl" and "alkoxy" denote linear or branched groups containing 1 to 6 carbon atoms, inclusive,
the terms "alkenyl" and "alkynyl" denote linear or branched groups containing 2 to 6 atoms, inclusive,
the term "cycloalkyl" denotes a group of 3 to 8 carbon atoms, inclusive,
the term "substituted" associated with the alkyl group means that this group is substituted with one or more substituents chosen from halogen, alkyl, hydroxyl, and alkoxy,
the term "substituted" associated with the "cycloalkyl" and "cycloalkylalkyl" radical means that this group is substituted with one or more groups chosen from halogen, alkyl, and oxo, and the enantiomers and diastereoisomers thereof.

2. A compound selected from those of claim 1, wherein,
R₁ represents alkyl,
R₁ represents (C₂-C₆)alkyl,
R₁ represents ethyl,
R₁ represents propyl, or
R₁ represents butyl,
A forms with the benzene ring to which it is attached, benzothiophene, R₂ represents hydrogen, or
R₂ represents alkyl,
R₃ represents a group R₃₁ as defined in formula (I), or
R₃ represents a group R₃₂ as defined in formula (I),
R₄ represents hydrogen,
R₄ represents alkyl,
R₄ represents cycloalkyl, or
R₄ represents alkenyl,
R₅ represents hydrogen,
R₅ represents alkyl, or
R₅ represents cycloalkyl,
X represents oxygen, or
X represents sulfur,
X' represents oxygen,
or X' represents sulfur.

3. A compound selected from those of claim 1, which corresponds to the formula:

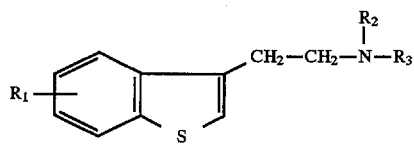

or

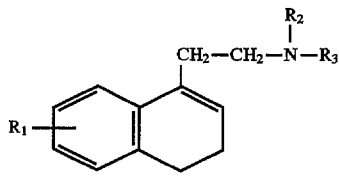

4. A compound as claimed in claim 1, which is N-[2-(5-ethylbenzothiophen-3-yl)ethyl]acetamide.

5. A pharmaceutical composition comprising a compound of formula (I) as claimed in claim 1, in combination with one or more pharmaceutically acceptable excipients.

6. A method of treating a mammal afflicted with a melatoninergic disorder comprising the step of administering to the said mammal an effective amount of a compound as claimed in claim 1 for alleviating the said condition.

7. A method of treating sleep disorders according to claim 6.

8. A compound as claimed in claim 1, which is (R,S) N-[2-(5-ethylbenzothiophen-3-yl)ethyl]cyclobutane-carboxamide.

9. A compound as claimed in claim 1, which is N-[2-(5-ethylbenzothiophen-3-yl)ethyl]butyramide.

10. A compound as claimed in claim 1, which is N-[2-(5-ethylbenzothiophen-3-yl)ethyl]propionamide.

11. A compound as claimed in claim 1, which is N-[2-(5-ethylbenzothiophen-3-yl)ethyl]valeramide.

12. A compound as claimed in claim 1, which is N-[2-(5-ethylbenzothiophen-3-yl)ethyl]cyclopropane-carboxamide.

13. A compound as claimed in claim 1, which is N-[2-(5-ethylbenzothiophen-3-yl)ethyl]-N'-propylurea.

14. A compound as claimed in claim 1, which is N-[2-(5-ethylbenzothiophen-3-yl)ethyl]-N'-methylurea.

* * * * *

UNITED STATES PATENT AND TRADEMARK OFFICE
CERTIFICATE OF CORRECTION

PATENT NO. : 5,693,665
DATED : Dec. 2, 1997
INVENTOR(S) : D. Lesieur; E. Fourmaintraux; P. Depreux; P. Delagrange; P. Renard; B. Guardiola-Lemaitre Page 1 of 2

It is certified that error appears in the above-indentified patent and that said Letters Patent is hereby corrected as shown below:

Column 2, lines 41,43,45,47,49&51: Insert a --,-- (comma) after the word "forms" in each line.

Column 2, lines 43,45,47,49&51: Insert a --,-- (comma) after the word "attached" in each line.

Column 6, line 18: "formula (IIia)" should read -- formula (IIIa) --.

Column 7, line 67: "formula (II/" at the end of the line, should read -- formula (II/a) --.

Column 8, line 1: Delete "a)" from the beginning of the line.

Column 17, line 64: "Ih" should read --1 h--.

Column 23, line 50: The line should read --7.68 ppm (multiplet, 1H):$H_4$ --.

Column 31, line 19: "$R^2$" should read -- $R_2$ --.

Column 32, line 27 (first line under formula): Insert -- $R_1$, $R_2$, and $R_3$ being defined in Claim 1. --.

UNITED STATES PATENT AND TRADEMARK OFFICE
CERTIFICATE OF CORRECTION

PATENT NO. : 5,693,665
DATED : Dec. 2, 1997
INVENTOR(S) : D. Lesieur; E. Fourmaintraux; P. Depreux; P. Delagrange; P. Renard; B. Guardiola-Lemaitre It is certified that error appears in the above-indentified patent and that said Letters Patent is hereby corrected as shown below:

Column 32, line 28: Delete the word "or".

Column 32, lines 29-35: Delete this second formula.

Column 32, line 39: Insert, before "comprising", -- useful in alleviating melatoninergic disorders --

Signed and Sealed this

Tenth Day of March, 1998

Attest:

BRUCE LEHMAN

*Attesting Officer*     *Commissioner of Patents and Trademarks*